(12) United States Patent
Gurusamy et al.

(10) Patent No.: US 7,635,353 B2
(45) Date of Patent: Dec. 22, 2009

(54) TRANSSEPTAL PUNCTURE NEEDLES AND NEEDLE ASSEMBLIES

(75) Inventors: Ravisankar Gurusamy, Eagan, MN (US); John D. Ockuly, Waikoloa, HI (US); Hans Schnellmann, Lausanne (CH); James A. Hassett, Eden Prairie, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 587 days.

(21) Appl. No.: 10/947,817

(22) Filed: Sep. 22, 2004

(65) Prior Publication Data
US 2006/0064062 A1 Mar. 23, 2006

(51) Int. Cl.
*A61M 5/178* (2006.01)
*A61M 5/32* (2006.01)
*A61B 17/34* (2006.01)

(52) U.S. Cl. .................. 604/170.03; 604/272; 606/185
(58) Field of Classification Search ............ 604/164.01, 604/170.03, 264, 272; 606/167, 184, 185
See application file for complete search history.

(56) References Cited

U.S. PATENT DOCUMENTS

| | | | |
|---|---|---|---|
| 5,281,218 A | 1/1994 | Imran | |
| 5,403,311 A | 4/1995 | Abele et al. | |
| 5,405,376 A | 4/1995 | Mulier et al. | |
| 5,431,649 A | 7/1995 | Mulier et al. | |
| 5,507,802 A | 4/1996 | Imran | |
| 5,628,734 A * | 5/1997 | Hatfalvi | 604/272 |
| 5,807,395 A | 9/1998 | Mulier et al. | |
| 5,906,613 A | 5/1999 | Mulier et al. | |
| 5,945,070 A * | 8/1999 | Kath et al. | 422/101 |
| 6,053,904 A * | 4/2000 | Scribner et al. | 604/527 |
| 6,958,056 B2 * | 10/2005 | Kadziauskas et al. | 604/272 |

OTHER PUBLICATIONS

International Standard: Steril Hypodermic Needles for Single Use, ISO Reference No. 7864:1993(E).

* cited by examiner

*Primary Examiner*—Nicholas D Lucchesi
*Assistant Examiner*—Victoria P Campbell
(74) *Attorney, Agent, or Firm*—Heimbecher & Assoc., LLC

(57) ABSTRACT

The instant invention is directed toward transseptal puncture needles and transseptal puncture needle assemblies. More specifically, it relates to curved transseptal puncture needles and needle assemblies that facilitate insertion through curved transseptal introducers. Each curved transseptal puncture needle includes a needle tip with a tangential back bevel configuration, a reverse tangential back bevel configuration, or a conical reverse bevel configuration. The axial orientation of the needle tip relative to the needle curvature, whether on the concave side or convex side of the curved transseptal puncture needle, provides additional benefits. The leading edge of the needle tip is located at a distal end of an inner needle tube, and the leading edge of the needle tip may be positioned away from an outer surface of the inner needle tube and adjacent to an inner surface of the inner needle tube.

35 Claims, 24 Drawing Sheets

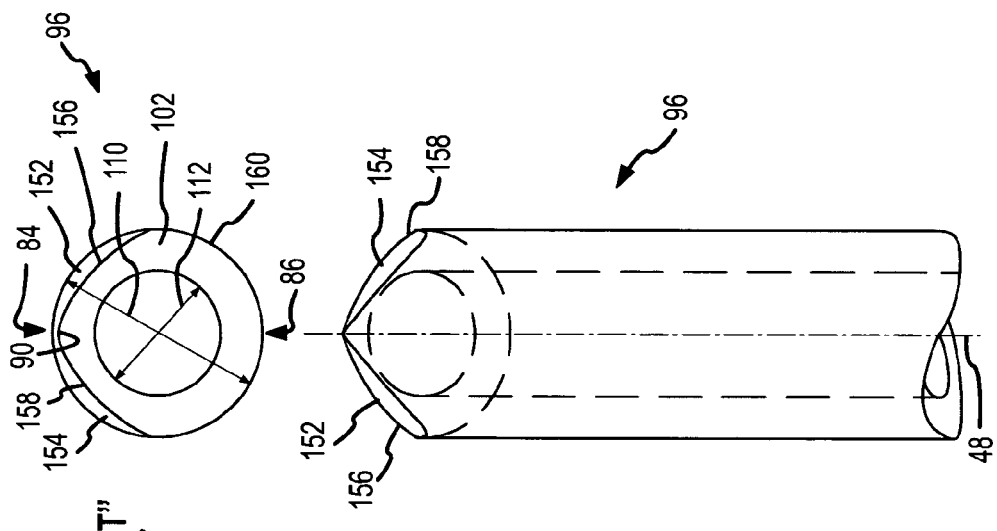
FIG. 7 "PRIOR ART"
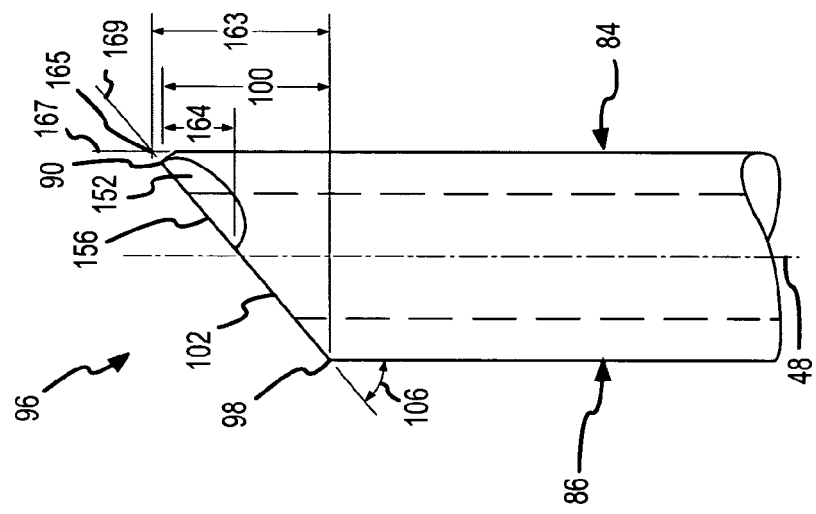
FIG. 9 "PRIOR ART"
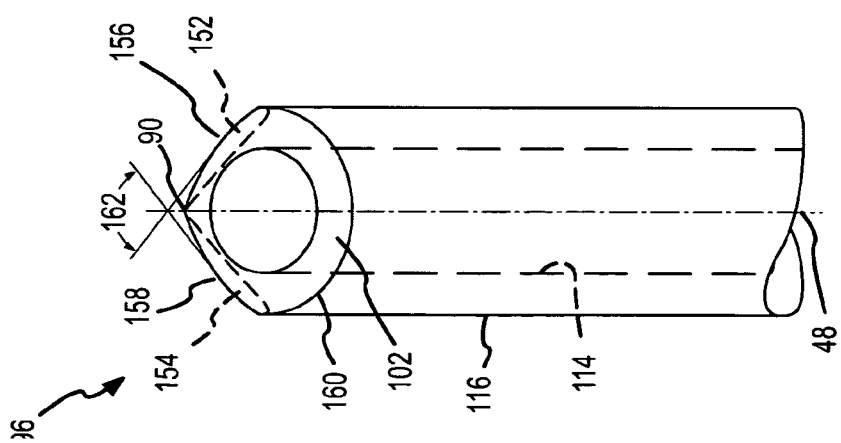
FIG. 8 "PRIOR ART"
FIG. 10 "PRIOR ART"

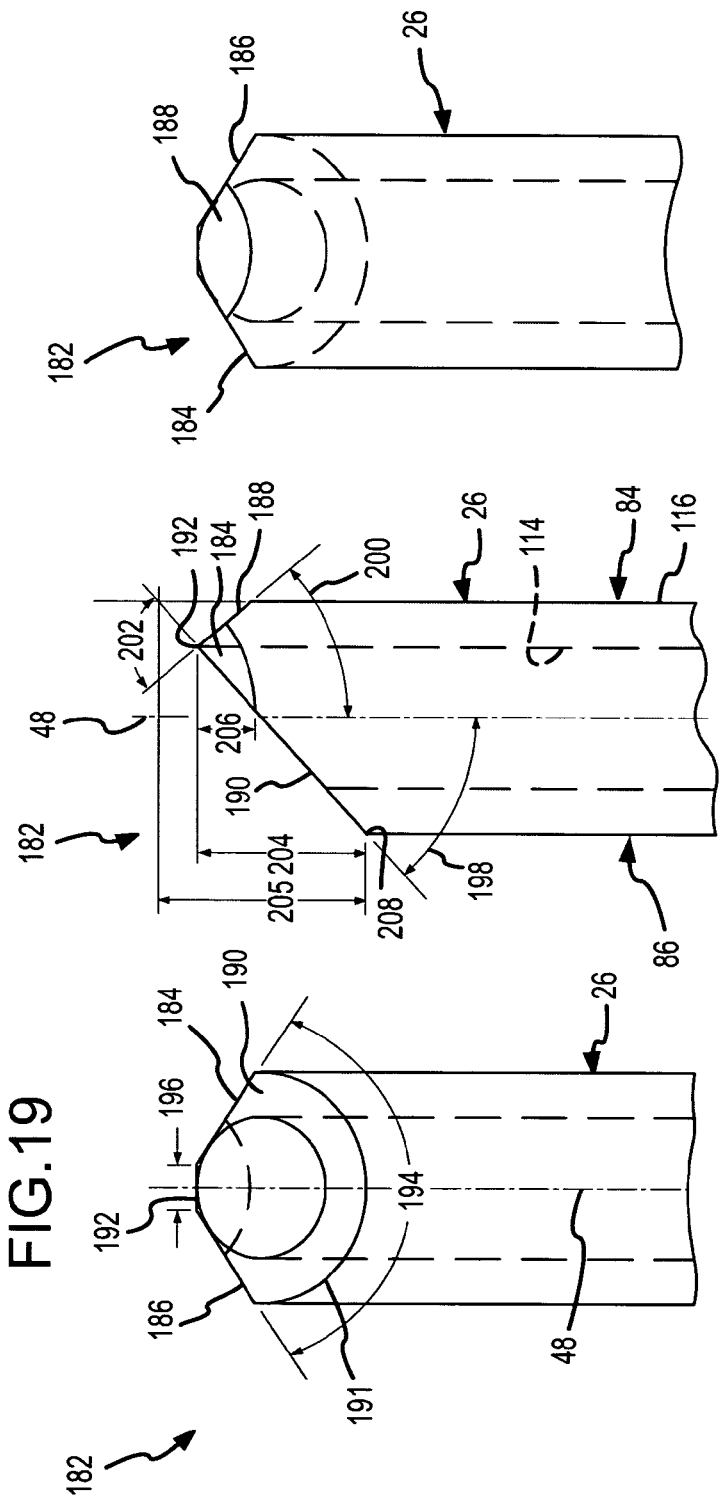

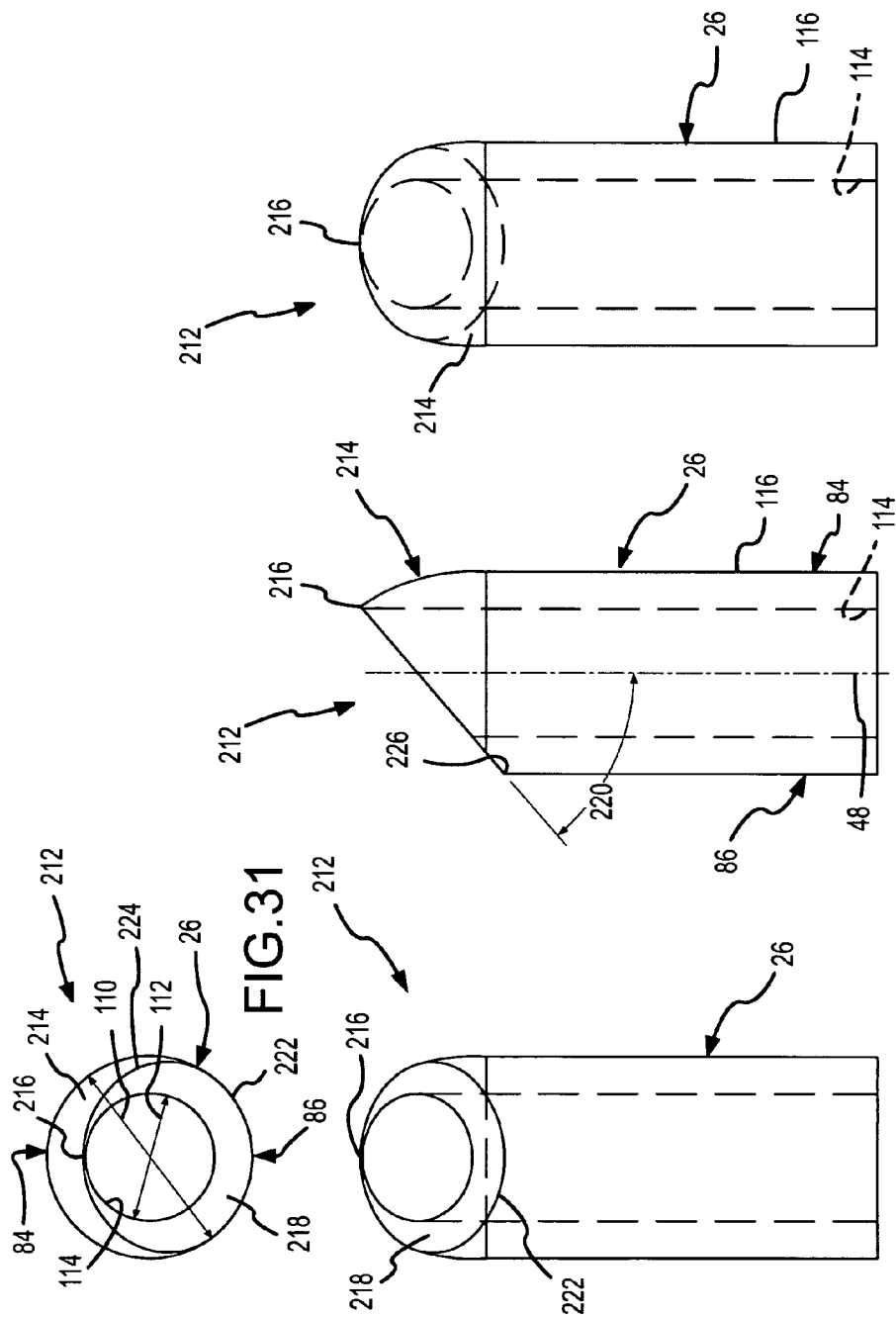

| Sample Identifier | Outer Needle Tube Dimensions OD/ID x L, mm (inches) | Inner Needle Tube Dimensions OD/ID x L, mm (inches) | Entrance Diameter at Proximal End of Inner Needle Tube, mm (inches) | Entrance Diameter at Proximal End of Outer Needle Tube, mm (inches) | Length of Conjoined Outer and Inner Needle Tubes, mm (inches) | Height of Overall Needle Curvature, mm (inches) | Radius of Overall Needle Curvature, mm (inches) | Length of Exposed Portion of Conjoined Inner and Outer Needle Tubes, mm (inches) | Works with These Sample Stylets (see Fig. 42) |
|---|---|---|---|---|---|---|---|---|---|
| a | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 715 ±2 (28.150 ±.078) | 20 ±0.2 (.787 ±.008) | 48 ±2 (1.89 ±.078) | 710 ±2 (27.953 ±.078) | B |
| b | 1.2/0.8 x 769 (.047/.0315 x 30.28) | 0.8/0.5 x 99 (.0315/.0197 x 3.90) | 0.7 ±0.05 (.028 ±.002) | 1.1 ±0.05 (.043 ±.002) | 783 ±2 (30.835 ±.078) | 55 ±0.2 (2.170 ±.008) | 54 ±2 (2.125 ±.078) | 778 ±2 (30.635 ±.078) | C |
| c | 1.1/0.7 x 551 (.043/.0276 x 21.69) | 0.7/0.4 x 99 (.0276/.0157 x 3.90) | 0.6 ±0.05 (.024 ±.002) | 1 ±0.05 (.039 ±.002) | 565 ±2 (22.244 ±.078) | 20 ±0.2 (.787 ±.008) | 48 ±2 (1.89 ±.078) | 560 ±2 (22.047 ±.078) | A |
| d | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 715 ±2 (28.150 ±.078) | 55 ±0.2 (2.170 ±.008) | 54 ±2 (2.125 ±.078) | 710 ±2 (27.953 ±.078) | B |
| e | 1.1/0.7 x 551 (.043/.0276 x 21.69) | 0.7/0.4 x 99 (.0276/.0157 x 3.90) | 0.6 ±0.05 (.024 ±.002) | 1 ±0.05 (.039 ±.002) | 565 ±2 (22.244 ±.078) | 19 ±0.2 (.746 ±.008) | 30 ±2 (1.193 ±.078) | 560 ±2 (22.047 ±.078) | A |
| f | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 985 ±2 (38.780 ±.078) | 55 ±0.2 (2.170 ±.008) | 54 ±2 (2.125 ±.078) | 980 ±2 (38.583 ±.078) | D |
| g | 1.2/0.8 x 881 (.047/.0315 x 34.69) | 0.8/0.5 x 99 (.0315/.0197 x 3.90) | 0.7 ±0.05 (.028 ±.002) | 1.1 ±0.05 (.043 ±.002) | 895 ±2 (35.236 ±.078) | 20 ±0.2 (.787 ±.008) | 48 ±2 (1.89 ±.078) | 890 ±2 (35.040 ±.078) | E |

Fig. 41

| Sample Identifier | Length of Working Portion of the Wire Plus Substantially Straight Support Section of the Handle Portion, mm (inches) | Handle Tube Dimensions OD/ID x L, mm (inches) | Entire Wire Dimensions OD x L, mm (inches) | Works with These Sample Needles (see Fig. 41) |
|---|---|---|---|---|
| A | 605 ±2 (23.819 ±.078) | 0.6/0.35 x 56 (.024/.014 x 2.205) | 0.3 x 640 (.012 x 25.197) | c, e |
| B | 755 ±2 (29.724 ±.078) | 0.7/0.4 x 56 (.028/.016 x 2.205) | 0.35 x 790 (.014 x 31.102) | a, d |
| C | 823 ±2 (32.402 ±.078) | 0.7/0.4 x 56 (.028/.016 x 2.205) | 0.35 x 858 (.014 x 33.779) | b |
| D | 1025 ±2 (40.354 ±.078) | 0.7/0.4 x 56 (.028/.016 x 2.205) | 0.35 x 1060 (.014 x 41.732) | f |
| E | 935 ±2 (36.811 ±.078) | 0.7/0.4 x 56 (.028/.016 x 2.205) | 0.35 x 970 (.014 x 38.190) | g |

Fig. 42

TRANSSEPTAL PUNCTURE NEEDLES AND NEEDLE ASSEMBLIES

BACKGROUND OF THE INVENTION a. Field of the Invention

The instant invention is directed toward transseptal puncture needles and transseptal puncture needle assemblies. More specifically, it relates to curved transseptal puncture needles and needle assemblies that facilitate insertion through curved transseptal introducers.

b. Background Art

Transseptal puncture needles are used by physicians who perform specialized invasive cardiology techniques. For example, it is known to access the left atrium using a transseptal approach for catheter ablation of arrythmogenic tissue. During such an approach, a physician uses a transseptal introducer and a long, curved needle for left atrial access from the venous system. The introducer, which is curved to facilitate access to a desired portion of the left-heart anatomy, includes a sheath and may include a separate dilator. The curved needle may be, for example, a stainless steel Brockenbrough curved needle or a trocar.

The curved needle is used to make the transseptal puncture after the curved transseptal introducer is used to guide the needle into position. In particular, once the transseptal introducer is in the right atrium, the distal tip of the guiding introducer is positioned against a puncture site, such as the fossa ovalis in the inter-atrial septal wall. The Brockenbrough needle is then advanced distally through the transseptal introducer beyond the distal end of the introducer until it punctures the fossa ovalis. If the introducer includes a dilator, the dilator may be advanced with a needle through the punctured fossa ovalis to prepare an access port through the septum and into the left atrium. Once the sheath has been seated across the septum and in the left atrium, the dilator, if present, and the needle may be withdrawn from the sheath. This sheath then provides lumenal access into the left atrium for direct insertion of, for example, a treatment or diagnostic catheter.

An example of an existing transseptal puncture needle assembly, which comprises the combination of a transseptal puncture needle and stylet, is available from Unimed SA of Lausanne, Switzerland under their part number UMEDST-1 or BRK-1, which is also known by St. Jude Medical, Daig Division, Inc. part number 20601. An example of an existing transseptal introducer is the Swartz SL4 introducer available from St. Jude Medical, Daig Division, Inc.

To facilitate insertion of the curved needle through the curved transseptal introducer, a stylet is inserted into the cannula of the needle. The stylet is a flexible rod that stiffens the curved needle and gives it form during its passage through the curved transseptal introducer.

In order to minimize the risk of inadvertently puncturing the left atrial wall just after crossing the septum, it is important that the transseptal puncture needle is sharp to reduce the amount of insertion force required. If excessive force is required to insert the needle through the introducer or to puncture the inter-atrial septum, the transseptal puncture needle may inadvertently puncture the atrial free wall, the aorta, the inferior vena cava, or the coronary sinus, for example.

BRIEF SUMMARY OF THE INVENTION

It is an object of the disclosed invention to provide an improved transseptal puncture needle and needle assembly. It is desirable to be able to insert a curved transseptal puncture needle or needle assembly, which is a needle plus its stylet, through a curved transseptal introducer without requiring undue force, while reducing scraping of the needle (particularly the needle tip) against the inner surface of the transseptal introducer to reduce the risk of removing particulate material during needle advancement inside of the introducer, and while avoiding extensive coring of the inter-atrial septum.

With the increasing need to use acutely (i.e., sharply) curved introducers to gain access to various portions of the left-heart anatomy, it is important that the shape of the needle tip and the axial orientation of the needle tip relative to the overall curvature of the needle be carefully considered.

In a first generation of the curved transseptal puncture needle according to the present invention, a needle tip with an existing tangential back bevel configuration is used, but has a new axial orientation. In particular, the puncture tip leading edge is axially oriented to be on the concave side of the curved transseptal puncture needle.

In subsequent generations of the curved transseptal puncture needle according to the present invention, which are discussed further below, the leading edge of the needle tip is located at a distal end of the inner needle tube, and the leading edge of the needle tip is located away from the outer surface of the inner needle tube and adjacent to the inner surface of the inner needle tube. In these generations of the curved transseptal puncture needle, the leading edge of the needle tip may be oriented along the convex side of the curved needle or the concave side of the curved needle.

In a second generation of the transseptal puncture needle according to the present invention, the needle tip has a reverse tangential back bevel configuration, which offsets its puncture tip leading edge to the inner surface of the inner needle tube. The puncture tip leading edge is oriented to be on either the convex side of the needle or the concave side of the needle. The reverse tangential back bevel configuration comprises a first tangential back bevel, a second tangential back bevel, and a puncture tip offset bevel, wherein the puncture tip offset bevel moves the puncture tip leading edge toward or to the inner surface of the inner needle tube.

In a third generation of the transseptal puncture needle according to the present invention, the needle tip has a conical reverse bevel configuration, which again offsets its puncture tip leading edge to the inner surface of the inner needle tube. The puncture tip leading edge is oriented to be on either the convex side of the needle or the concave side of the needle.

In another form, the present invention comprises an elongated, curved transseptal puncture needle comprising a needle proximal end and a needle distal end. The needle distal end comprises a working portion including an inner needle tube and an outer needle tube. The inner needle tube and the outer needle tube are conjoined. Both the inner needle tube and the outer needle tube comprise a proximal end and a distal end. The proximal end of the inner needle tube is inserted into the distal end of the outer needle tube, creating an embedded portion and an exposed portion of the inner needle tube, and creating a circumscribing portion and a nonoverlapping portion of the outer needle tube. The conjoined inner and outer needle tubes define a conjoined outer surface including an outer surface of the outer needle tube plus an outer surface of the exposed portion of the inner needle tube. The curved transseptal puncture needle further comprising a needle tip at the distal end of the inner needle tube, and the needle tip comprises a puncture tip leading edge, a puncture tip trailing edge, and a wedge surface extending between the puncture tip leading edge and the puncture tip trailing edge. The conjoined inner and outer needle tubes have a first side and a second side. The first side comprises the portion of the conjoined outer surface extending longitudinally along and including that portion of an outer surface of the inner needle tube that extends most closely adjacent to the puncture tip leading edge. The second side of the conjoined inner and outer needle tubes comprises that portion of the conjoined outer surface that is radially offset from the first side of the conjoined inner and outer needle tubes by 180°.

In yet another form, the present invention comprises a device for use by individuals performing specialized invasive techniques. The device comprises a curved transseptal puncture needle and a curved transseptal introducer through which the curved transseptal puncture needle is inserted. The a curved transseptal puncture needle comprises a first side, a second side offset from the first side by 180°, and a needle tip. The needle tip further comprises a puncture tip leading edge, a puncture tip trailing edge, and a wedge surface extending between the puncture tip leading edge and the puncture tip trailing edge. The needle tip has a needle tip configuration that is either a tangential back bevel, a reverse tangential back bevel, or a conical reverse bevel. The curved transseptal introducer comprises a convex side and a concave side offset from the convex side by 180°. In this form of the invention, the curved transseptal puncture needle has a selected axial orientation relative to the curved transseptal introducer.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 7 is an end or top view of the prior art needle tip of FIGS. 5 and 6.

FIG. 8 is a front view of the prior art needle tip of FIGS. 5-7.

FIG. 9 is a side view of the prior art needle tip of FIGS. 5-8, the opposite side view being a mirror image thereof.

FIG. 10 is a rear view of the prior art needle tip of FIGS. 5-9.

FIG. 19 is an end or top view of the needle tip depicted in FIGS. 17 and 18.

FIG. 20 is a front view of the needle tip depicted in FIGS. 17-19.

FIG. 21 is a side view of the needle tip depicted in FIGS. 17-20, the opposite side view being a mirror image thereof.

FIG. 22 is a rear view of the needle tip depicted in FIGS. 17-21.

FIG. 31 is an end or top view of the needle tip depicted in FIGS. 29 and 30. [0047] FIG. 32 is a front view of the needle tip depicted in FIGS. 29-31.

FIG. 33 is a side view of the needle tip depicted in FIGS. 29-32, the opposite side view being a mirror image thereof.

FIG. 34 is a rear view of the needle tip depicted in FIGS. 29-33.

FIG. 41 depicts a table of dimensions for seven sample transseptal puncture needles according to the present invention.

FIG. 42 depicts a table of dimension for five sample stylets according to the present invention.

DETAILED DESCRIPTION OF THE INVENTION

Figure 1:
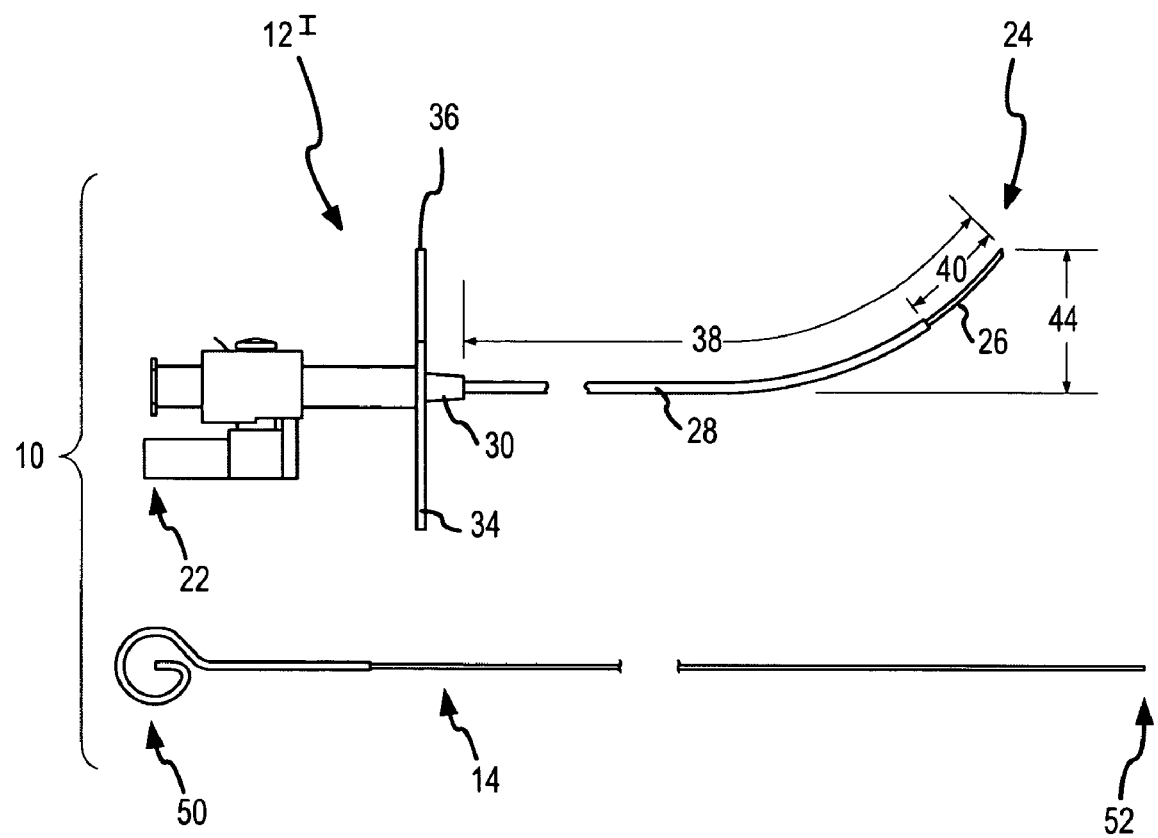
FIG. 1 is a fragmentary, side view of a transseptal puncture needle assembly according to a first embodiment of the present invention, including a transseptal puncture needle and a stylet.
Figures 11, 12:
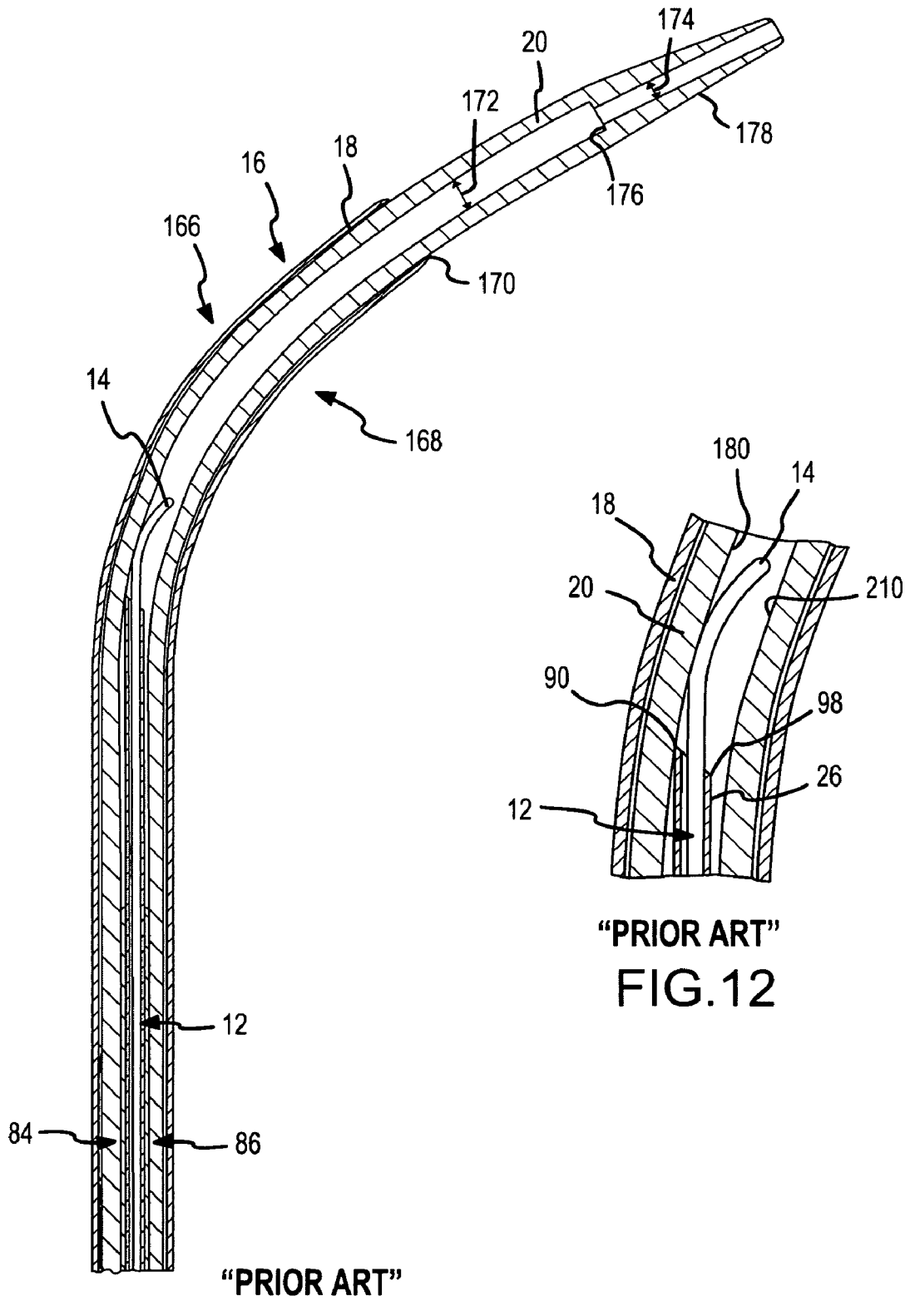
FIG. 11 is a fragmentary, cross-sectional view of a curved transseptal puncture needle having the prior art tip configuration depicted in FIGS. 5-10 and a prior art axial orientation when partially inserted through a curved transseptal introducer.
FIG. 12 is an enlarged, fragmentary, cross-sectional view of a portion of FIG. 11 to better show interaction between the puncture tip leading edge and the inner surface of the dilator.

The present invention comprises curved transseptal puncture needles 12 (e.g., 12$^I$ in FIG. 1) and needle assemblies 10 (i.e., the combination of a curved transseptal puncture needle 12$^I$ and its stylet 14 as shown in FIG. 1) that facilitate insertion through curved transseptal introducers 16 (i.e., sheaths, or sheath 18 and dilator 20 combinations as shown in, for example, FIG. 11). The needle assemblies 10 and introducers 16 permit, for example, left atrial access from the venous system for catheter diagnosis and treatment (e.g., ablation of arrhythmogenic cardiac tissue). Each curved transseptal puncture needle 12 has a specific tip configuration and axial orientation, the combination of which is designed to facilitate low-force, smooth insertion through the introducer 16 while reducing the risk of introducing dilator particulate removed by the needle tip into a patient's left heart or blood stream, and while reducing the amount of coring that may occur during puncture of the patient's inter-atrial septum.

FIG. 1 depicts a transseptal puncture needle assembly 10 according to the present invention. The transseptal puncture needle assembly 10 comprises a transseptal puncture needle 12 and a stylet 14. The transseptal puncture needle 12 is elongated, having a proximal end 22 and a distal end 24. The working portion of the needle comprises an inner needle tube 26 and an outer needle tube 28, which are conjoined as explained further below. The conjoined inner and outer needle tubes 88 (FIG. 4) are united with a mounting collar 30 that may be seen to good advantage in FIG. 1. For example, the proximal end 32 (FIG. 4) of the conjoined inner and outer needle tubes 88 may be press fit into the mounting collar 30 (e.g., approximately 5 mm) and may be affixed in position by an adhesive. In one embodiment, epoxy is used to join the proximal end 32 of the conjoined inner and outer needle tubes 88 to the mounting collar 30 by applying epoxy to a depth of approximately 0.2 mm. Between the distal end 24 of the transseptal puncture needle 12 and the mounting collar 30 is a shield 34 having a shield point 36. The shield point 36, which is more clearly shown in FIG. 3, indicates the direction of curvature of the transseptal puncture needle 12 (i.e., the conjoined inner and outer needle tubes 88.)

Length 38 is the length of the exposed portion of the conjoined inner and outer needle tubes 88. Similarly, length 40 is the length of the straight, exposed portion 42 (FIG. 4) of the inner needle tube 26. The length 40 of this straight, exposed portion 42 of the inner needle tube 26 is approximately 15±0.2 mm (i.e., 0.590±0.008 inches) in one embodiment of the present invention. Height 44 is the overall height of needle curvature. Sample values for each of these dimensions are presented in the table 46 of FIG. 41. The table 46 of FIG. 41, which is explained further below, includes additional dimensions also. For example, the radius of overall needle curvature is presented in the eighth column from the left in FIG. 41. These sample values for the radii of overall needle curvature refer to the approximate curvature along a needle centerline or longitudinal axis 48 (see FIG. 4) of the curved portion (visible in, for example, FIGS. 1 and 3) of the transseptal puncture needle. This represents the curvature of the rightmost portion of the transseptal puncture needle 12 depicted in FIG. 1. As shown to good advantage in FIG. 1, the stylet 14 also includes a proximal end 50 and a distal end 52.

Figure 2:
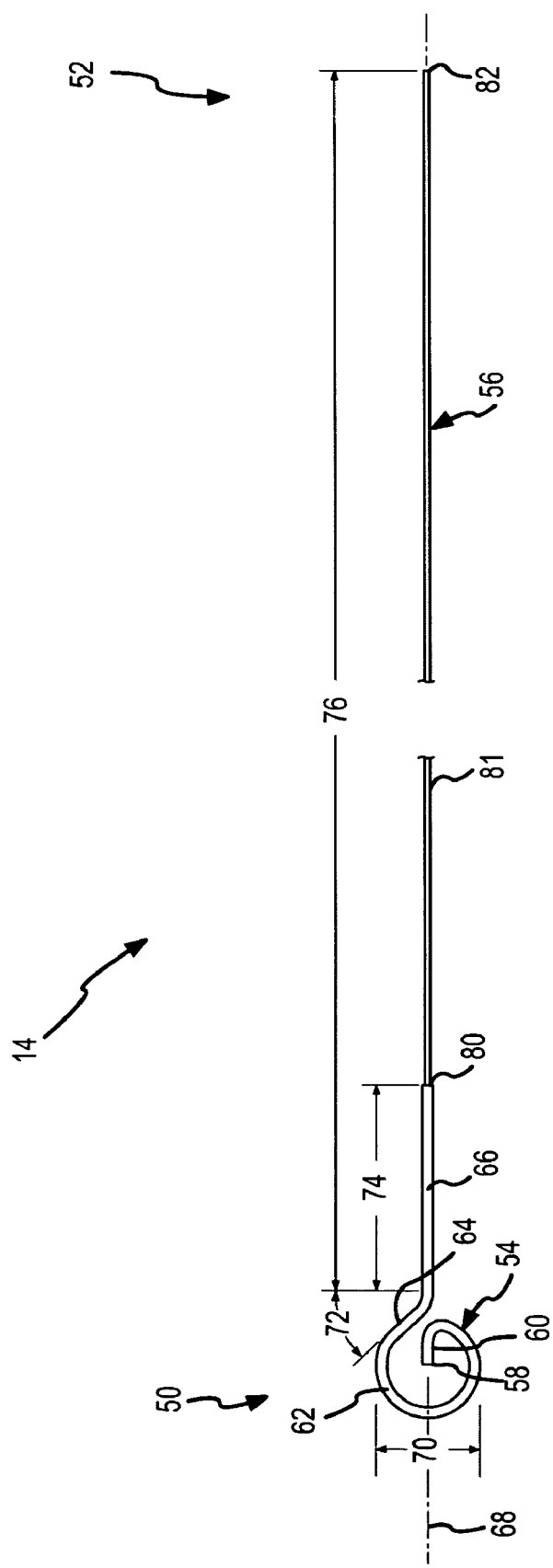
FIG. 2 is an enlarged, fragmentary view of the stylet depicted in FIG. 1.

Referring next to FIG. 2, additional details concerning the stylet 14 are discussed next. The proximal end 50 of the stylet includes a handle portion 54, and the distal end 52 of the stylet includes a working portion 56. The handle portion 54 is in the shape of a stylized letter "G" starting at a trailing end 58, continuing with a free end section 60, an arcuate section 62, a transition section 64, and a substantially straight support section 66. The trailing end 58 and free end section 60 are aligned with a stylet centerline 68, and the handle portion 54 overall is essentially centered about the stylet centerline 68. The overall hand height 70 is 10±2 mm (i.e., 0.399 inches) in one embodiment of the present invention. In the depicted embodiment, the transition section 64 connects the arcuate section 62 to the substantially straight support section 66 at a transition angle 72 defined as the angle between the vertical line depicted in FIG. 2 and a line parallel to the longitudinal centerline (not shown) of the transition section. In one embodiment of the present invention, the transition angle 72 is 45°. The transition section joins the substantially straight support section when the transition section 64 curves into the substantially straight support section 66. In one embodiment of the present invention, the transition section 64 curves into the substantially straight support section 66 along a radius of curvature of 2.5 mm (i.e., 0.100 inches). In one embodiment of the present invention, the length 74 of the substantially straight support section 66 is 21 mm (i.e., 0.827 inches). The combined length 76 of the working portion 56 and the substantially straight support section 66 varies depending upon the specific application for the transseptal puncture needle 12. Possible combined length dimensions (i.e., the length of the working portion 56 of the wire, which is the exposed portion of the wire, plus the length of the substantially straight support section 66 of the handle portion 54) for five sample stylets are presented in the second column of the table 78 in FIG. 42.

The handle portion 54 may be made from, for example, AISI 304 stainless steel tubing. Sample dimensions for sections of tubing that may be shaped into the handle portion 54 are presented in the third column of the table 78 of FIG. 42. In the third column, the dimensions are presented as OD/ID×L, wherein "OD" is the outer diameter of the tubing, "ID" is the inner diameter of the tubing, and "L" is the length of the tubing. All dimensions are provided once in millimeters with the same information presented parenthetically in inches. The sample outer diameter dimensions presented in the third column in FIG. 42 have the following tolerances in one embodiment: ±0.01 mm (i.e., ±0.0004 inches). Similarly, the tolerances for the sample inner diameter dimensions presented in the third column of FIG. 42 are as follows: +0.03 mm and −0 mm (i.e., +0.001 inches and −0 inches). The substantially straight support section 66 of the handle portion 54 terminates distally at a leading end 80. Preferably, there is no play between the handle portion 54 and the working portion 56 at the leading end 80 and break edges are present (i.e., the leading end 80 is preferably blunt with rounded edges).

Continuing to refer to FIG. 2, the working portion 56, which is the exposed part of a stylet wire 81 that extends into the handle portion 54, terminates distally at a leading end 82 that is blunt with rounded edges. In one embodiment of the present invention, the wire 81 comprising the working portion 56 is AISI 302 stainless steel wire. Some possible overall lengths for this wire are presented in the fourth column of the table 78 of FIG. 42. The dimensions in each sample entry in the fourth column are presented as OD×L, where "OD" is the outer diameter of the wire, and "L" is the total length of the entire wire, including the working portion 56 and the portion embedded in the handle portion 54. These dimensions are again provided in millimeters with their equivalents in inches presented in parentheticals. The length dimensions provided in the fourth column of FIG. 42 have the following tolerances +0 mm and −0.015 mm (i.e., +0 inches and −0.0006 inches). The fifth column of the table presented in FIG. 42 provides compatibility information for the sample needles from FIG. 41 with which the stylets of FIG. 42 may be used. For example, the stylet with sample identifier "A" in FIG. 42 may be used with sample needles "c" or "e" of FIG. 41. For the sample stylet embodiments presented in FIG. 42 and depicted in FIG. 2, approximately 56 mm of the wire resides within the tubing comprising the handle portion 54. Thus, a distal portion of the wire comprises the working portion 56 of the stylet 14, and a proximal portion of the wire extends into the handle portion 54 of the stylet 14 along and proximally past the proximal end of the substantially straight support section 66 of the handle portion 54. Since a portion of the wire comprising the working portion 56 of the stylet 14 extends into at least a part of the handle portion 54 of the stylet 14, the outer diameter of the wire must be selected to fit within the inner diameter of the tubing comprising the handle portion 54. In the sample information presented in FIGS. 41 and 42, the outer diameter of the wire is selected to be 0.05 mm smaller than the inner diameter of the tubing comprising the handle portion 54. Thus, the wire fits into the tubing, but the play is minimized between the wire and the tubing.

The table 78 presented in FIG. 42 provides dimension data for five sample stylets according to the present invention. The first column presents a sample identifier. The second column presents the length of the working portion of the wire (i.e., the exposed portion of the wire) plus the length of the substantially straight support section 66 of the handle portion 54. In other words, the sample lengths presented in the second column of the table of FIG. 42 represents the distance from the leading end 82 of the stylet wire, which coincides with the distal end 52 of the stylet 14, to the proximal end of the substantially straight support section 66 of the handle portion 54 of the stylet 14. The third column represents sample dimensions for the tubing from which the handle portion 54 may be formed. These numbers represent the possible dimensions for a section of tubing that may be shaped to form the handle portion 54. The number to the left of the slash represents the outer diameter of this tubing, the number to the right of the slash represents the inner diameter of this tubing, and the third number represents the length of the tubing. The dimensions are provided in millimeters, with the corresponding dimensions in inches provided parenthetically. The fourth column of FIG. 42 provides dimension information for sample wires, with the first dimension being the outer diameter of the wire and the second dimension being the overall length of the wire. Again, the numbers are provided in millimeters with the inch equivalents following in parentheticals. The sample length dimensions in this fourth column represent the overall length of the wire that comprises the working portion 56 of the stylet 14, including the part of the wire that is embedded in the hollow handle portion 54. It should be noted that samples "B," "D," and "E" are considered dimensions for an adult stylet. Sample "A" presents dimensions for a pediatric stylet, and sample "C" presents dimensions for an atrial mapping and ablation system (AMAS) stylet. The length of exposed wire (i.e., the length of the working portion 56 of the stylet 14 to the right of the leading end 80 of the substantially straight support section 66 of the handle portion 54 as depicted in FIG. 2) for the sample dimensions presented above or as follows: 584 mm for stylet "A," 734 mm for stylet "B," 802 mm for stylet "C," 1004 mm for stylet "D," and 914 mm for stylet "E."

Figure 3:
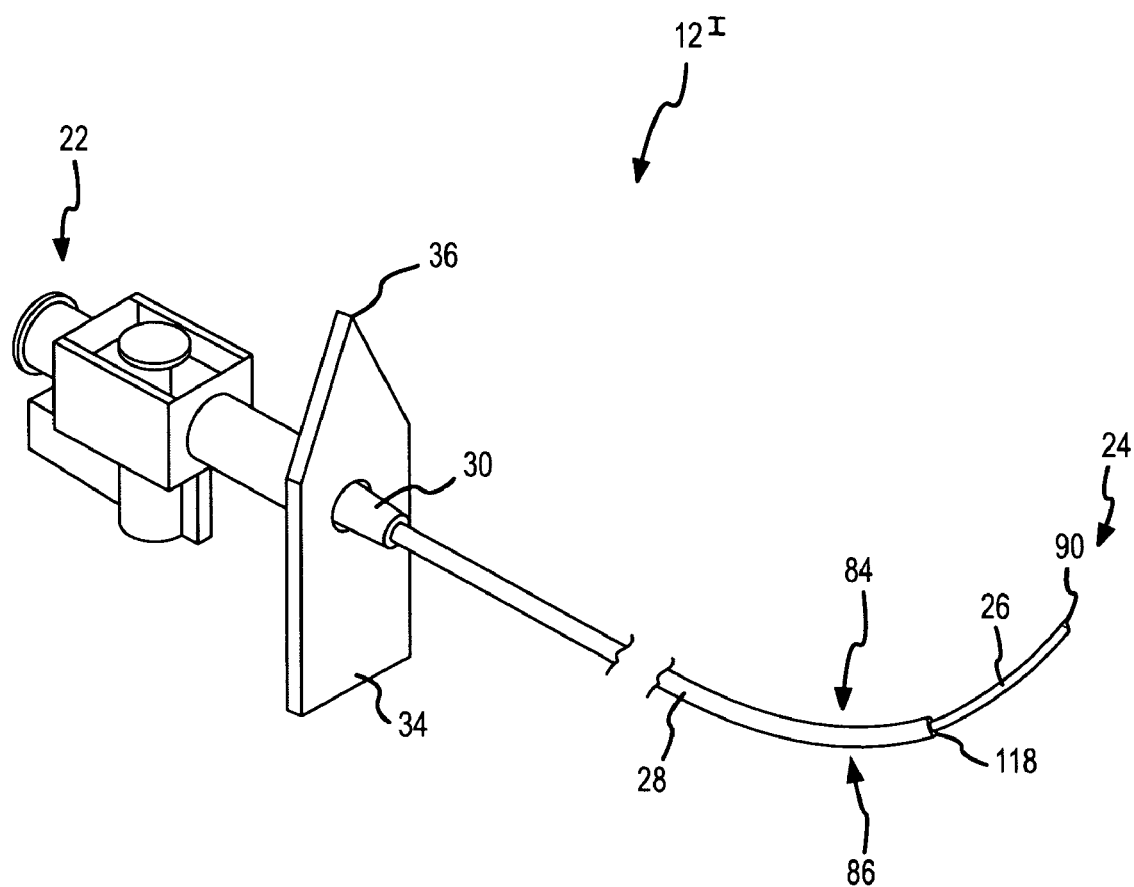
FIG. 3 is a slightly enlarged, fragmentary, isometric view of the curved transseptal puncture needle depicted in FIG. 1.

FIG. 3 is a slightly enlarged, fragmentary isometric view of the curved transseptal puncture needle 12$^I$ depicted in FIG. 1. This depiction of the transseptal puncture needle clearly shows how the shield point 36 indicates the direction of curvature of the needle 12$^I$. As shown in FIG. 3, the transseptal puncture needle 12$^I$ has a first side 84 in a second side 86. The first side 84 comprises the outer surface of the conjoined inner and outer needle tubes 88 (FIG. 4) extending longitudinally along and including that portion of the outer surface of the inner needle tube 26 that extends most closely adjacent to a puncture tip leading edge 90. The fist side 84 may also be seen to good advantage in FIG. 4. The second side 86 is that portion of the outer surface of the conjoined inner and outer needle tubes 88 that is radially offset from the first side 84 by 180°. Again, the second side 86 of the transseptal puncture needle 12$^I$ is also clearly labeled in FIG. 4.

Figure 4:
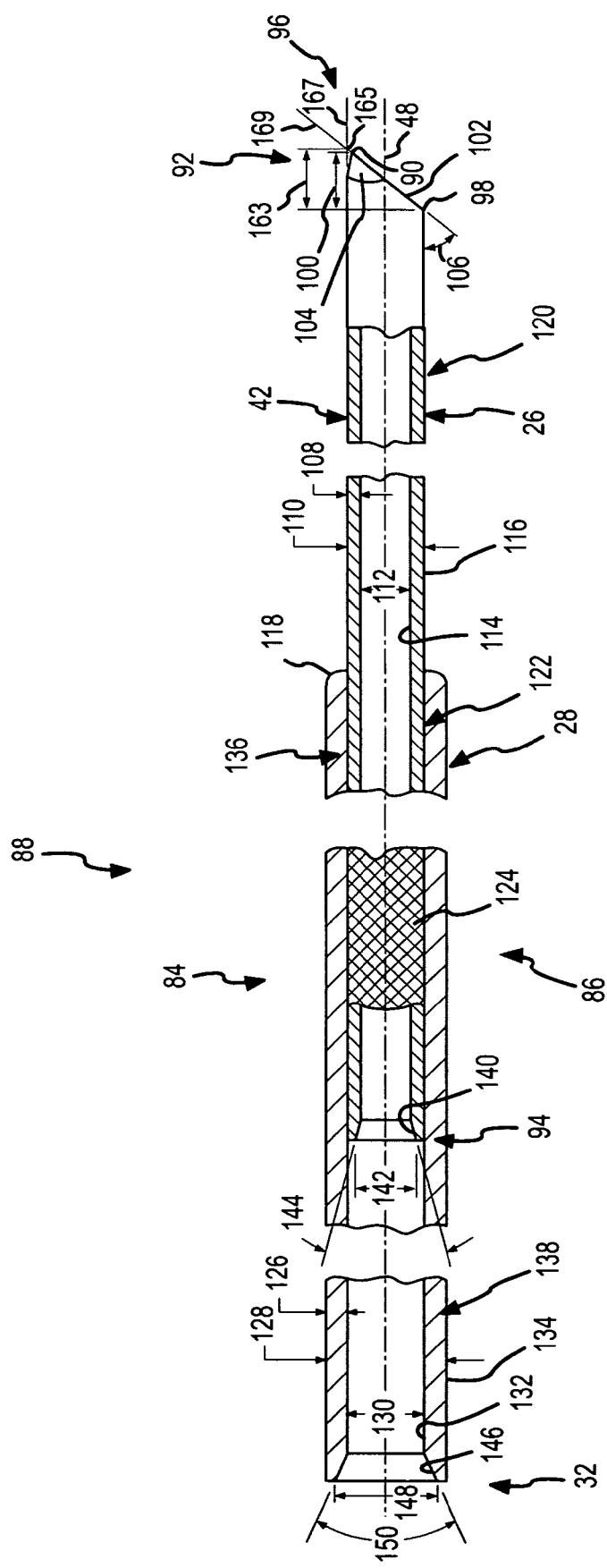
FIG. 4 is a fragmentary view in partial cross-section of the basic configuration of the conjoined inner needle tube and outer needle tube of the curved transseptal puncture needle, and shows the needle with the needle tip configuration and orientation according to the first embodiment of the present invention, which is also depicted in FIGS. 1 and 3.

FIG. 4 is an enlarged, isometric view of the conjoined inner and outer needle tubes 88 of the transseptal needle 12$^I$ depicted in FIGS. 1 and 3 broken away from the remaining parts of the transseptal needle 12$^I$ for clarity. The outer needle tube 28 and the inner needle tube 26 may each comprise AISI 304 stainless steel tubing. The inner needle tube 26 comprises a distal end 92 and a proximal end 94. The distal end 92 of the inner needle tube 26 includes a needle tip 96 having the puncture tip leading edge 90 and a puncture tip trailing edge 98. The distance measured parallel to the needle's centerline 48 from the puncture tip leading edge 90 to the puncture tip trailing edge 98 is the needle tip length 100, and a tip wedge surface 102 is defined between the puncture tip leading edge 90 and the puncture tip trailing edge 98. The wedge surface 102 may be finished, for example, by sandblasting. In the embodiment depicted in FIG. 4, the needle tip 96 has a prior art configuration including a tangential back bevel 104, which may be better seen in FIGS. 5-10. The specifics of this tip configuration are explained further below.

In the needle tip depicted in FIGS. 4-10, the tip wedge surface 102 forms a wedge surface angle 106 of approximately 50°. The inner needle tube 26 has an inner tube thickness 108, an inner tube outer diameter 110, and an inner tube inner diameter 112. The inner needle tube 26 also comprises an inner surface 114 and an outer surface 116. Since the proximal end 94 of the inner needle tube 26 is inserted into a distal end 118 of the outer needle tube 28, the inner needle tube 26 also comprises an exposed portion 120 and an embedded portion 122. In an embodiment of the present invention, the embedded portion 122 of the inner needle tube 26 is approximately eighty-three millimeters long and is secured within the outer needle tube 28 by adhesive 124 as described further below.

The outer needle tube 28 extends from the distal end 118 of the outer needle tube 28 to a proximal end 32 of the outer needle tube 28. Similar to the inner needle tube 26, the outer needle tube 28 has an outer tube thickness 126, an outer tube outer diameter 128, an outer tube inner diameter 130, an inner surface 132, and an outer surface 134. Since the outer needle tube 28 does overlap with the embedded portion 122 of the inner needle tube 26, the outer needle tube 28 further comprises a circumscribing portion 136, which is the portion of the outer needle tube 28 that extends around the embedded portion 122 of the inner needle tube 26, and a nonoverlapping portion 138, which is the remainder of the outer needle tube 28. The distal end 118 of the outer needle tube 28 is blunt with rounded edges.

The proximal end 94 of the inner needle tube 26 is configured similarly to the proximal end 32 of the outer needle tube 28. In particular, a frustal entrance surface 140 extends from the inner surface 114 of the inner needle tube 26 to the proximal end 94 of the inner needle tube 26. Where this frustal entrance surface 140 meets the proximal end 94 of the inner needle tube 26, an entrance diameter 142, which is slightly small than the outer diameter 110 of the inner needle tube 26 is present. The walls of the frustal entrance surface 140 form an entrance angle 144 of approximately 60° in one embodiment. Similarly, a frustal entrance surface 146 extends from the inner surface 132 of the outer needle tube 28 to the proximal end 32 of the outer needle tube 28, thereby defining an entrance diameter 148 that is slightly smaller than the outer diameter 128 of the outer needle tube 28. Again, the surfaces of the frustal entrance surface 146 at the proximal end 32 of the outer needle tube 28 form an entrance angle 150 of approximately 60°.

Thus, FIG. 4 depicts the basic configuration of the conjoined inner and outer needle tubes 88 of the transseptal puncture needle. This basic configuration is used for all of the transseptal puncture needles 12 (FIGS. 11-13), 12$^I$ (FIGS. 1, 3, 4, and 14-16), 12$^{II}$ (FIGS. 23-25), 12$^{III}$ (FIGS. 26-28), 12$^{IV}$ (FIGS. 35-37), 12$^V$ (FIGS. 38-40) described herein, even though FIG. 4 depicts a specific configuration for the puncture tip leading edge 90 that applies only to the first embodiment of the present invention. The remainder of this specification thus does not redescribe the baseline configuration of the conjoined inner and outer needle tubes 88, and focuses on the configuration of the needle tip at the distal end 92 of the inner needle tube 26 and the axial orientation of the puncture tip leading edge 90 relative to the overall curvature of the transseptal puncture needle 12 along its needle centerline 48.

To join the embedded portion 122 of the inner needle tube 26 within the circumscribing portion 136 of the outer needle tube 28, the embedded portion 122 may be sandblasted and epoxy may be applied to approximately 68 mm (2.68 inches) of the embedded portion 122. Thus, of the approximately 83 mm of overlap, epoxy may be applied to approximately 68 mm.

As mentioned above, the table 46 of FIG. 41 provides dimension data for seven sample transseptal puncture needles according to the present invention. Each of these needles could have one of the tips 96, 182, 212 discussed herein and would be used with an appropriately dimensioned introducer 16 and stylet 14. The first column of the table presented in FIG. 41 is a sample identifier. The second column of the table presents outer needle tube dimensions. These outer needle tube dimensions are represented as OD/ID×L, wherein "OD" is the outer diameter 128 of the outer needle tube 28, "ID" is the inner diameter 130 of the outer needle tube 28, and "L" is the overall length of the outer needle tube. The tolerance for the noted outer needle tube 28 outer diameters 128 is ±0.015 mm (i.e., ±0.0006 inches). Similarly, the inner diameter 130 dimensions presented in FIG. 41 for the outer needle tube 28 have tolerances of +0.04 mm and −0 mm (i.e., +0.0015 inches and −0 inches). The third column of the table presented in FIG. 41 represents sample inner needle tube dimensions. In the third column, the dimensions are again presented as OD/ID×L, wherein "OD" is the outer diameter 110 of the inner needle tube 26, "ID" is the inner diameter 112 of the inner needle tube 26, and "L" is the overall length of the sample inner needle tubes. With regard to the inner needle tube dimensions presented in FIG. 41, the outer diameters 110 presented are ±0.01 mm (i.e., ±0.004 inches) in one embodiment of the present invention. The tolerances for the inner diameters 112 of the inner needle tube 26 are +0.03 mm and −0 mm (i.e., +0.001 inches and −0 inches). In another embodiment or sample, the inner needle tubes are 98±2 mm (i.e., 3.858±0.078 inches).

The fourth column of the table 46 presented in FIG. 41 presents sample data for the entrance diameter 142 at the proximal end 94 of the inner needle tube 26. These sample entrance diameters 142 are presented as length in millimeters±a tolerance value. The equivalent dimensions are presented parenthetically in inches. The fifth column of the same table presents sample entrance diameter 148 information at the proximal end 32 of the outer needle tube 28. Again, this data is presented as length in millimeters±a tolerance value in millimeters, with the corresponding dimensions in inches presented parenthetically. The sixth column of the table presents sample information concerning the overall length of the conjoined outer and inner needle tubes 88, measured from the puncture tip leading edge 90 to the proximal end 32 of the outer needle tube 28. This sample length data is presented as a value in millimeters±a tolerance in millimeters, with the corresponding dimensions presented parenthetically in inches.

The seventh column of table 46 (FIG. 41) presents sample dimensions for the height 44 of the overall needle curvature (see FIG. 1), presented as length in millimeters±a tolerance value in millimeters with the equivalent dimensions in inches presented parenthetically. The eighth column of the table 46 presented in FIG. 41 presents sample dimensions for the radius of overall needle curvature. These values represent the approximate radius of curvature of the needle 12 and are presented as a value in millimeters±a tolerance in millimeters with the corresponding dimensions in inches provided parenthetically. The ninth column of this table presents sample dimensions for the length 38 of the exposed portion of the conjoined inner and outer needle tubes 88 (i.e., the overall length from the distal side of the mounting collar 30 to the puncture tip leading edge 90. These sample lengths 38 are presented in millimeters with a tolerance value also provided in millimeters. Equivalent dimensions in inches are provided parenthetically. The tenth column of the table presented in FIG. 41 ties this information to that provided for stylets in FIG. 42. For example, the needle having sample identifier "a" in FIG. 41 works with the stylet having sample identifier "B" in FIG. 42. It should also be noted that samples "a," "d," "f," and "g" presented in FIG. 41 are considered adult transseptal puncture needles. Samples "c" and "e" are considered pediatric transseptal puncture needles, and sample "b" is an AMAS needle.

Figure 5:
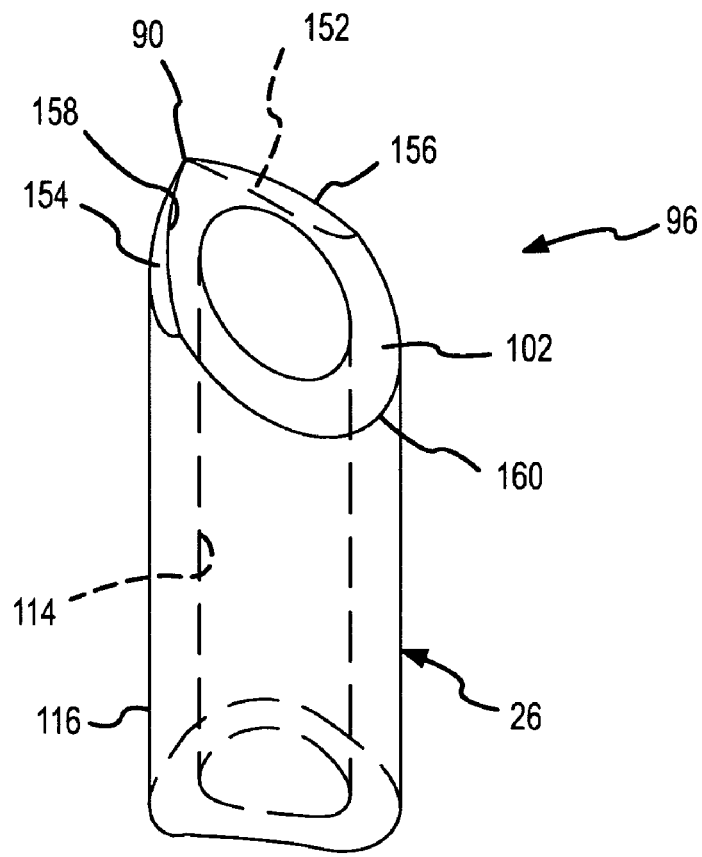
FIG. 5 is an enlarged, isometric view of a transseptal puncture needle having a prior art needle tip with a tangential back bevel configuration.
Figure 6:
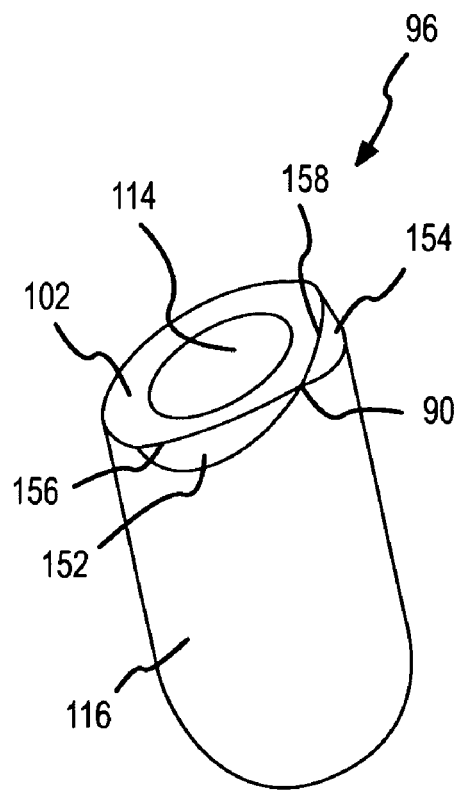
FIG. 6 is a second enlarged, isometric view of the prior art needle tip of FIG. 5.

FIGS. 5-10 depict a needle tip 96 having a prior art configuration. In particular, the needle tip 96 depicted in these figures has a tangential back bevel configuration, comprising a first tangential back bevel 152 and a second tangential back bevel 154. As shown in FIG. 5, which is an enlarged, isometric view of the prior art needle tip 96, the needle tip includes a puncture tip leading edge 90 and a wedge surface 102. A first cutting edge 156 is defined where the first tangential back bevel 152 meets the wedge surface 102, and a second cutting edge 158 is defined where the second tangential back bevel 154 meets the wedge surface 102. The outer surface 116 of the inner needle tube 26 and the inner surface 114 of the inner needle tube 26 are also labeled in FIG. 5. FIG. 6 is a second enlarged, isometric view of the same prior art needle tip 96. This figure shows the same features just described with reference to FIG. 5 from a different angle.

FIG. 7 is an end or top view of the prior art needle tip 96 depicted in FIGS. 4-6. As depicted in this figure, the wedge surface 102 is defined by an arcuate edge 160 that joins the first cutting edge 156 and the second cutting edge 158. The inner diameter 112 of the inner needle tube 26 is noted. Similarly, the outer diameter 110 of the inner needle tube 26 is noted. According to the third column in the table 46 of FIG. 41, if the inner diameter 112 is 0.5 mm, the outer diameter 110 may be 0.8 mm, and if the inner diameter 112 is 0.4 mm, the outer diameter 110 may be 0.7 mm. Thus, the inner needle tube thickness 108 (FIG. 4) is 0.15 mm for these embodiments. Clearly, however, other diameter combinations are contemplated by the present invention. At the twelve o'clock position in FIG. 7 is the first side 84, which, as discussed above comprises the outer surface (i.e., the outer surface 134 of the outer needle tube 28 plus the outer surface 116 of the exposed portion 120 of the inner needle tube 26) of the conjoined inner and outer needle tubes 88 most closely adjacent to the puncture tip leading edge 90. As also discussed above, the second side 86 is offset from the first side 84 by 180°. Thus, the second side 86 is at the six o'clock position in FIG. 7.

FIG. 8 is a front view of the needle tip 96 depicted in FIGS. 4-7. This view clearly shows the needle longitudinal axis 48 and shows an inter-bevel angle 162 between the first tangential back bevel 152 and the second tangential back bevel 154. In this embodiment of the needle tip 96, the inter-bevel angle 162 is approximately 114°.

FIG. 9 is a side view of the needle tip 96. As shown in FIG. 9, the needle tip length 100, which is also depicted in FIG. 4, is the distance from the puncture tip leading edge 90 to the puncture tip trailing edge 98 measured in a direction parallel to the needle longitudinal axis 48. The needle tip 96 also includes a point length 163, which is the distance measured parallel to the needle longitudinal axis 48 between the puncture tip trailing edge 98 and a point 165 that is offset 180° from the puncture tip trailing edge 98 (similar to the puncture tip leading edge 90) and that also is on the projected outer surface 167 of the inner needle tube 26 where a projected wedge surface line 169 intersects the projected outer surface 167. When extended, the projected wedge surface line 169 passes through the puncture tip trailing edge 98, the needle longitudinal axis 48, the puncture tip leading edge 90, and the point 165.

In the needle tip 96 depicted in FIGS. 8-10, the point length 163 is approximately 0.67 mm (i.e., 0.026 inches). The first tangential back bevel 152 and the second tangential back bevel 154 each has a bevel length 164 as shown in FIG. 9. In this embodiment, the bevel length 164 is desirably 30-50% of the point length 163. For example, when the point length 163 is 0.67 mm, the bevel length 164 may be approximately 0.3 mm. FIG. 10 is a rear view of the needle tip 96 depicted in FIGS. 5-9 and clearly shows that with this tangential back beveled configuration, the first and second tangential back bevels (152, 154), although not visible in the front view (FIG. 8) of the needle tip 96, are clearly visible in the rear view.

FIG. 11 is a fragmentary, cross-sectional view of a curved transseptal puncture needle 12 having the prior art tip configuration 96 depicted in FIGS. 5-10 and a prior art axial orientation relative to the curved transseptal introducer 16 through which it is being inserted. The curved transseptal introducer 16 has a convex side 166 and a concave side 168. The introducer 16 shown includes both a sheath 18 and a dilator 20, but the curved needles of the present invention may also be used with introducers that only have sheaths. As depicted in FIG. 11, the dilator 20 is extending from a distal end 170 of the sheath 18. The extended portion of the dilator necks down, from a first internal diameter 172 to a second internal diameter 174, creating an annular needle stop 176, as also mentioned below in connection with FIG. 13. The dilator 20 includes a frustal or tapered distal end 178. As shown in FIG. 11, in this prior art orientation of the curved transseptal puncture needle 12, the first side 84 of the needle 12 is on the convex curvature of the needle and its second side 86 is on the concave curvature of the needle. Thus, when the transseptal puncture needle 12 is forced through the introducer 16 as depicted in FIG. 11, the first side 84 of the needle 12 rides against the convex side 166 of the introducer 16, and the second side 86 of the needle 12 rides against the concave side 168 of the introducer 16.

As most clearly depicted in FIG. 12, since the first side 84 of the transseptal puncture needle 12 includes the puncture tip leading edge 90, when the needle 12 is forced through the introducer 16, the puncture tip leading edge 90 of the needle 12 scrapes along the inner surface 180 of the dilator 20 at the dilator's convex side 166 (the convex side 166 of the dilator 20 is, obviously, the same as the convex side 166 of the introducer 16). As a result, the transseptal puncture needle 12 is difficult to insert through the introducer 16 and is prone to remove dilator particulate as the needle 12 is advanced. This particulate material may undesirably end up in a patient's heart or blood stream.

Figure 13:
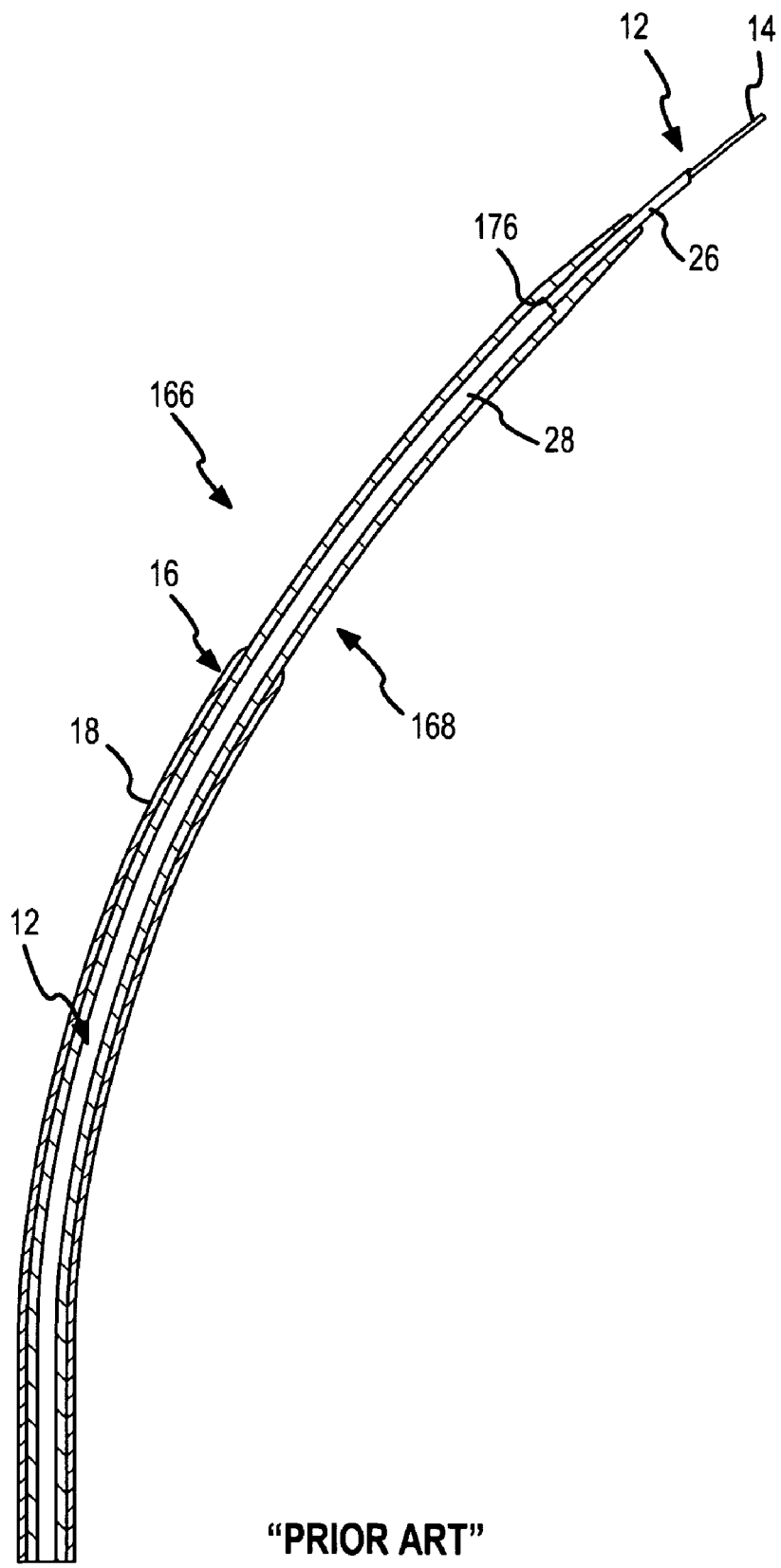
FIG. 13 is a fragmentary, cross-sectional view similar to FIG. 11, but depicting the curved transseptal puncture needle fully inserted against the annular needle stop of the curved transseptal introducer with the stylet still in place.

FIG. 13 is similar to FIG. 11, but depicts the needle 12 after it has been fully inserted against the annular needle stop 176 of the curved transseptal introducer 16. The annular needle stop 176 helps prevent the physician from pushing the needle 12 too far through the introducer 16, which would otherwise cause an excessive portion of the transseptal puncture needle 12 to extend beyond the distal end of the dilator 20. From a comparison of FIG. 13 with FIG. 11, it is apparent that in some configurations, full insertion of the transseptal puncture needle 12 into the introducer 16 may cause the introducer 16 to straighten slightly. In other words, the introducer 16 is more sharply angled or curved in FIG. 11, where the transseptal puncture needle 12 is partially inserted in the introducer 16, than in FIG. 13, where the transseptal puncture needle 12 is fully inserted in the introducer 16. Thus, with the prior art needle tip configuration 96 and orientation depicted in FIGS. 11-13, the puncture tip leading edge 90 is closely adjacent to the outer surface 116 of the inner needle tube 26 and is oriented closely adjacent to the convex side 166 of the introducer 16. Thus, both the configuration and the axial orientation of the puncture tip 96 may contribute to possible removal of particulate material from the dilator 20 by the puncture tip leading edge 90.

Figures 14, 15:
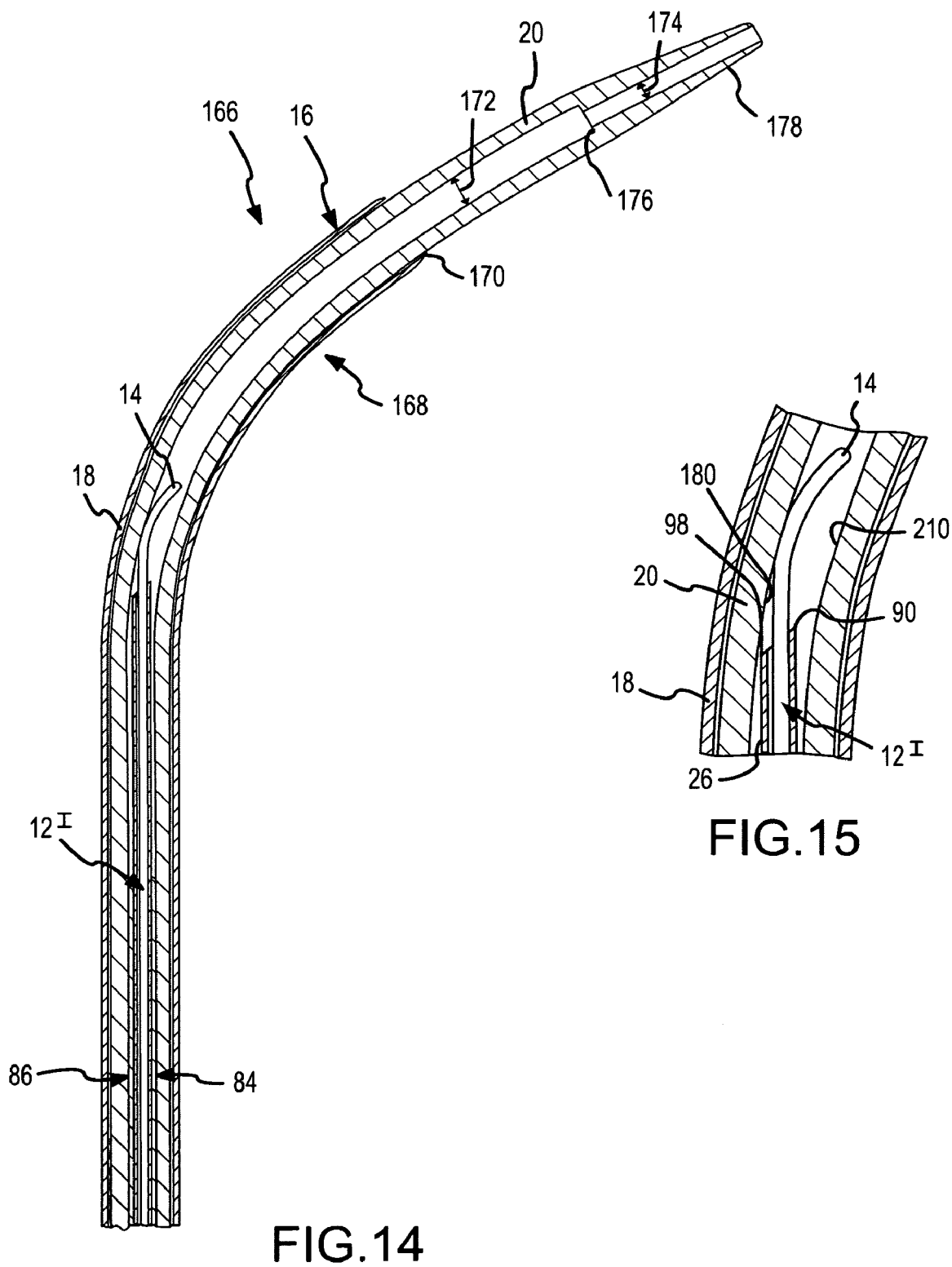
FIG. 14 is a fragmentary, cross-sectional view of a curved transseptal puncture needle having the prior art tip configuration depicted in FIGS. 5-10 and an axial orientation according to the first embodiment of the present invention, when partially inserted through a curved transseptal introducer.
FIG. 15 is an enlarged, fragmentary, cross-sectional view of a portion of FIG. 14 to better show the interaction between the puncture tip leading edge and the inner surface of the dilator.
Figure 16:
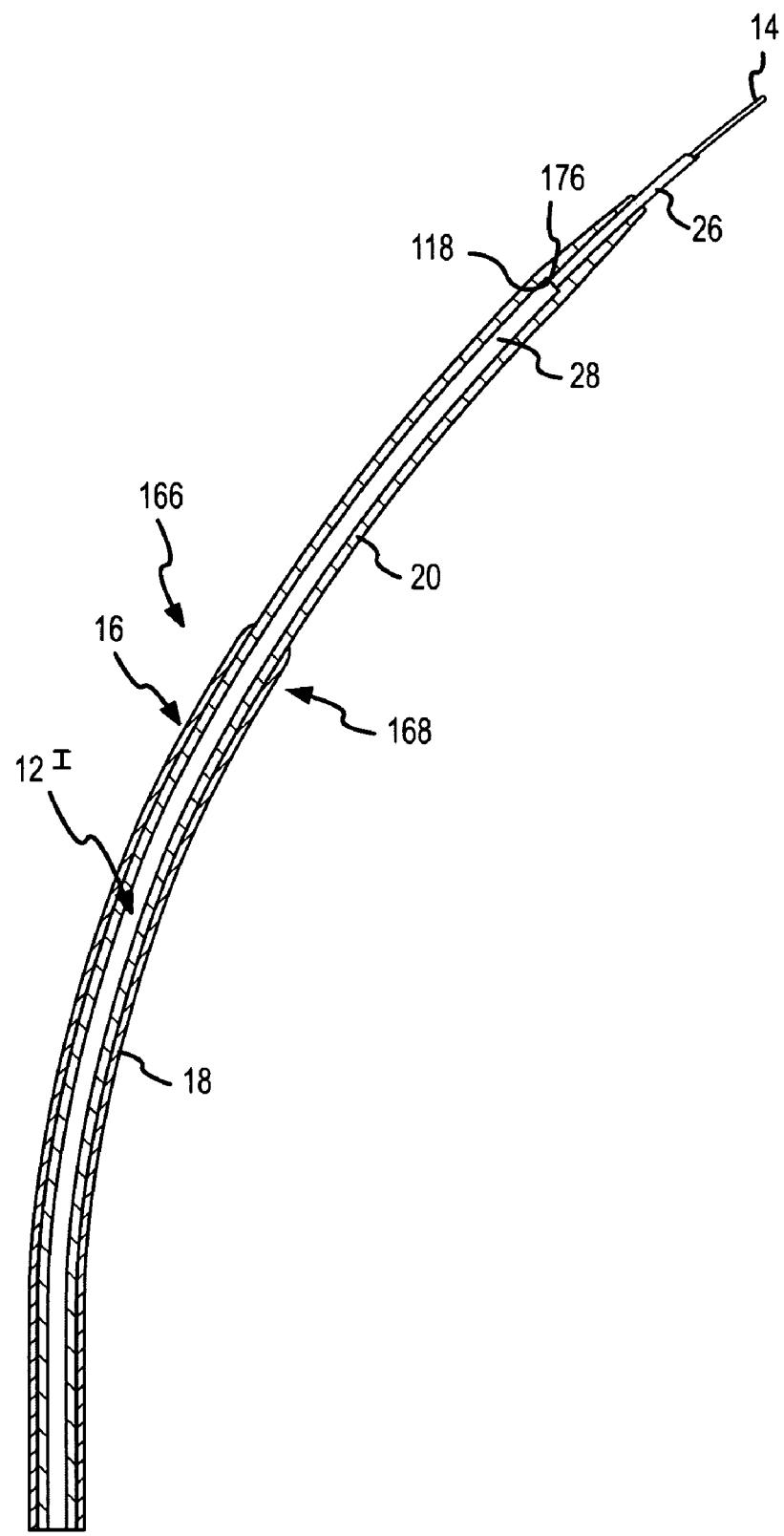
FIG. 16 is a fragmentary, cross-sectional view similar to FIG. 14, but depicting the curved transseptal puncture needle fully inserted against the annular needle stop of the curved transseptal introducer with the stylet still in place.

FIGS. 14-16 depict a first embodiment of a transseptal puncture needle 12' according to the present invention. In the embodiment of FIGS. 14-16, the prior art needle tip 96 of, for example, FIGS. 4-10 is again used. However, the axial orientation of the transseptal puncture needle 12$^I$ relative to the introducer 16 has been rotated 180° from the prior art orientation. FIG. 14 is a fragmentary, cross-section view of the curved transseptal puncture needle 12$^I$ according to the first embodiment of the present invention partially inserted through the dilator 20 of the introducer 16. As may be better seen from FIG. 15, which is an enlarged, fragmentary cross-sectional view of a portion of FIG. 14, the puncture tip leading edge 90 is less likely to remove particulate material from the inner surface of the dilator 20 in this new axial orientation. In particular, as shown in FIG. 15, it is the puncture tip trailing edge 98 (on the second side 86 of the needle 12$^I$) that impacts the inner surface 180 of the dilator 20 on the dilator's convex side 166. In this orientation, although the puncture tip trailing edge 98 may drag along the inner surface 180 of the convex side 166 of the dilator 20, it is less likely that particulate material will be scrapped from the inner surface of the dilator 20 in this configuration than it is in the prior art orientation depicted in FIGS. 11-13. FIG. 16 depicts the transseptal puncture needle 12$^I$ of FIGS. 14 and 15 fully seated against the annular needle stop 176.

Figure 17:
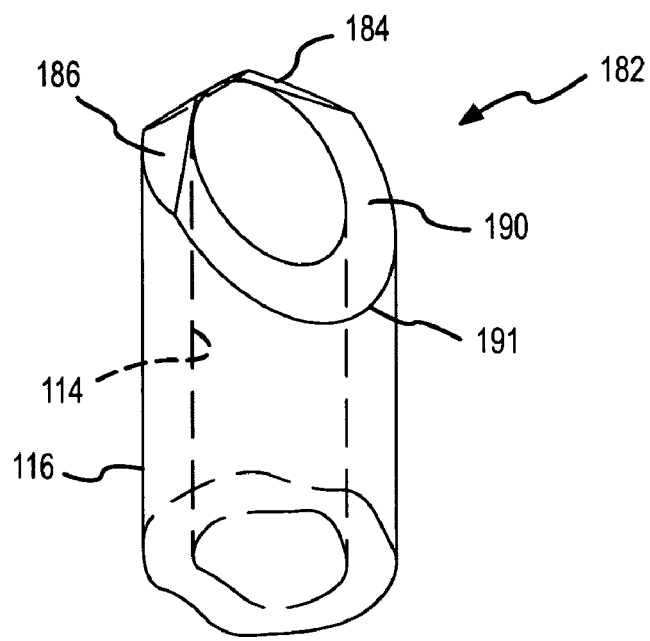
FIG. 17 is an enlarged, isometric view of a needle tip with a reverse tangential back bevel configuration used in a second embodiment and a third embodiment of the present invention.
Figure 18:
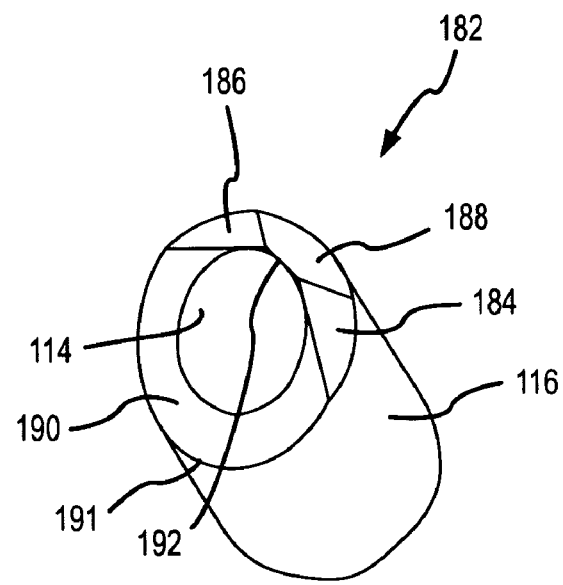
FIG. 18 is a second enlarged, isometric view of the needle tip depicted in FIG. 17.

FIGS. 17-22 are enlarged views of a needle tip 182 that is used in a second embodiment 12$^{II}$ and in a third embodiment 12$^{III}$ of the present invention. This needle tip 182 has a reverse tangential back bevel configuration with three bevels 184, 186, 188 in addition to a wedge surface 190. The three bevels include a first tangential back bevel 184, a second tangential back bevel 186, and a puncture tip offset bevel 188. FIG. 17 is an isometric view looking generally at the front and one side of the needle tip 182. The outer surface 116 of the inner needle tube 26 and the inner surface 114 of the inner needle tube 26 are both labeled in FIG. 17. The wedge surface 190 for this particular configuration of the needle tip 182 again includes an arcuate edge 191. This embodiment is thus superficially similar to the needle tip 90 depicted in FIGS. 5-10, but as explained further below, the puncture tip offset bevel 188 has been added to move the puncture tip leading edge 192 (see, e.g., FIGS. 18-21) from the outer surface 116 of the inner needle tube 26 to the inner surface 114 of the inner needle tube 26, which provides some advantages described below. FIG. 18 is a second enlarged, isometric view of the needle tip 182 depicted in FIG. 17 from a slightly different perspective.

FIG. 19 is an end or top view of the needle tip 182 depicted in FIGS. 17 and 18. The inner diameter 112 and the outer diameter 110 of the needle tip 182 are again labeled as they were in FIG. 7. As clearly shown in FIG. 19, the puncture tip offset bevel 188 moves the puncture tip leading edge 192 toward the inner surface 114 of the inner needle tube 26 of the transseptal puncture needle. This needle tip 182 is used for the curved transseptal puncture needle according to the second embodiment 12$^{II}$ (see FIGS. 23-25) and the third embodiment 12$^{III}$ (see FIGS. 26-28) of the present invention.

FIG. 20 is a front view of the needle tip 182 depicted in FIGS. 17-19. As shown in this figure, an inter-bevel angle 194 of approximately 120° exists between the first tangential back bevel 184 and the second tangential back bevel 186. As also clearly visible in FIG. 20, the puncture tip leading edge 192 has a puncture tip leading edge width 196, which may be approximately 0.2 mm. If the outer diameter 110 of the inner needle tube 26 is 0.8 mm, for example, the puncture tip leading edge width 196 is approximately one-quarter of the outer diameter 110 of the inner needle tube 26 of the transseptal puncture needle 12$^{II}$ or 12$^{III}$. FIG. 20 also shows the longitudinal axis 48.

FIG. 21 is a side view of the needle tip 182 depicted in FIGS. 17-20 and provides additional dimension and configuration information. In particular, the wedge surface angle 198 is again approximately 50°. The offset bevel angle 200 is approximately 40° in this embodiment. The intersection angle 202 between the wedge surface 190 and the puncture tip offset bevel 188 is approximately 90° in this embodiment. The needle tip 182 also has a needle tip length 204 and a point length 205. The needle tip length 204 may be, for example, 0.53 mm (i.e., 0.021 inches), and the point length 205 may be, for example, 0.55 mm (i.e., 0.022 inches). The bevel length 206 of the first and second tangential back bevels 184, 186, respectively, is again targeted to be approximately 30-50% of the point length 205. The puncture tip trailing edge 208 is also clearly visible in FIG. 21. As shown to good advantage in FIG. 22, the puncture tip offset bevel 188 extends off the rear side of the needle tip 182. As shown best by FIGS. 19 and 21, the puncture tip offset bevel 188 aligns the puncture tip leading edge 192 with the inner surface 114 of the inner needle tube 26 of the transseptal puncture needle 12$^{II}$ or 12$^{III}$.

Figures 23, 24:
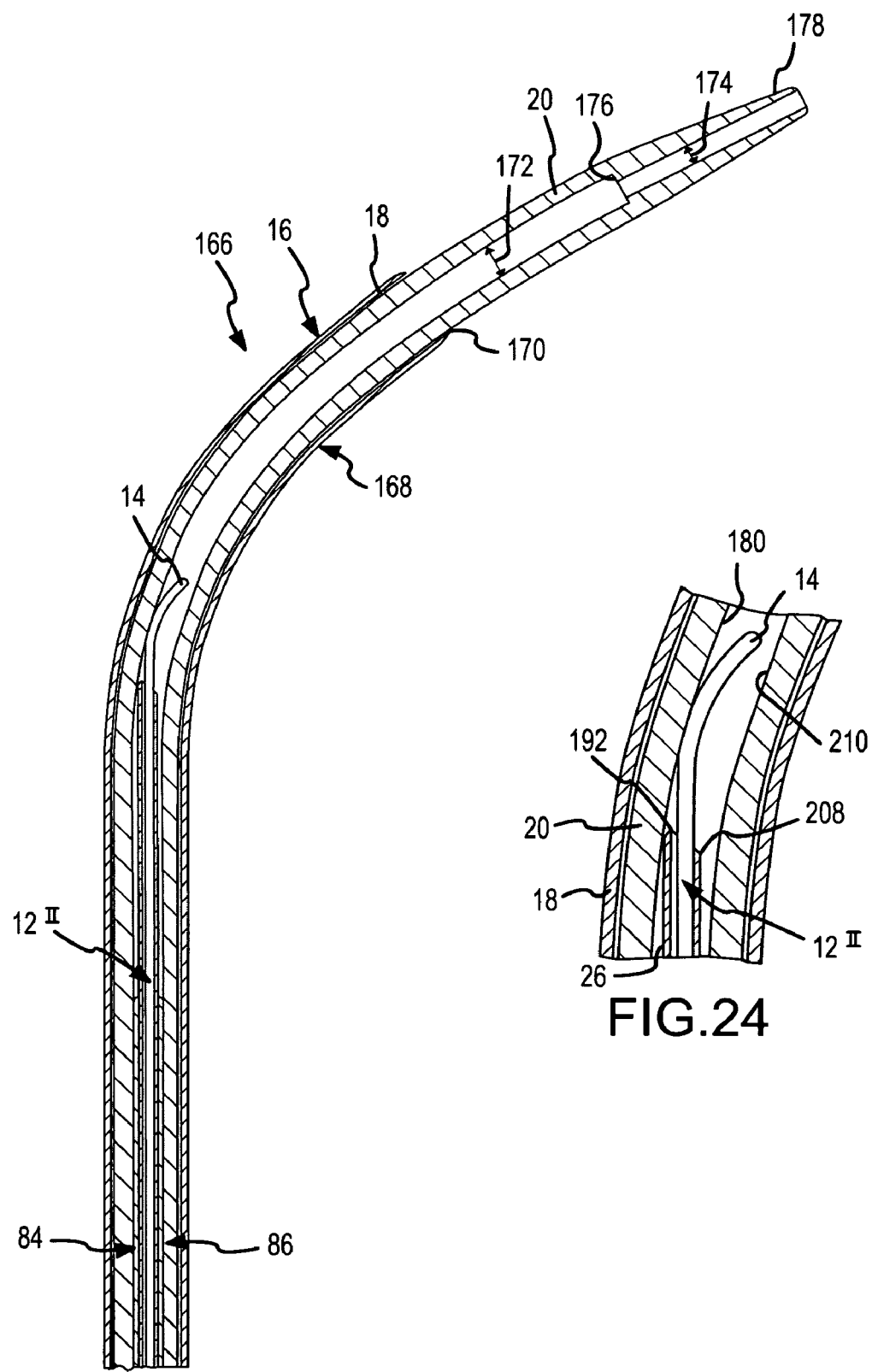
FIG. 23 is a fragmentary, cross-sectional view of a curved transseptal puncture needle having the tip configuration depicted in FIGS. 17-22 and an axial orientation according to the second embodiment of the present invention, when partially inserted through a curved transseptal introducer.
FIG. 24 is an enlarged, fragmentary, cross-sectional view of a portion of FIG. 23 to better show the interaction between the puncture tip leading edge and the inner surface of the dilator.
Figure 25:
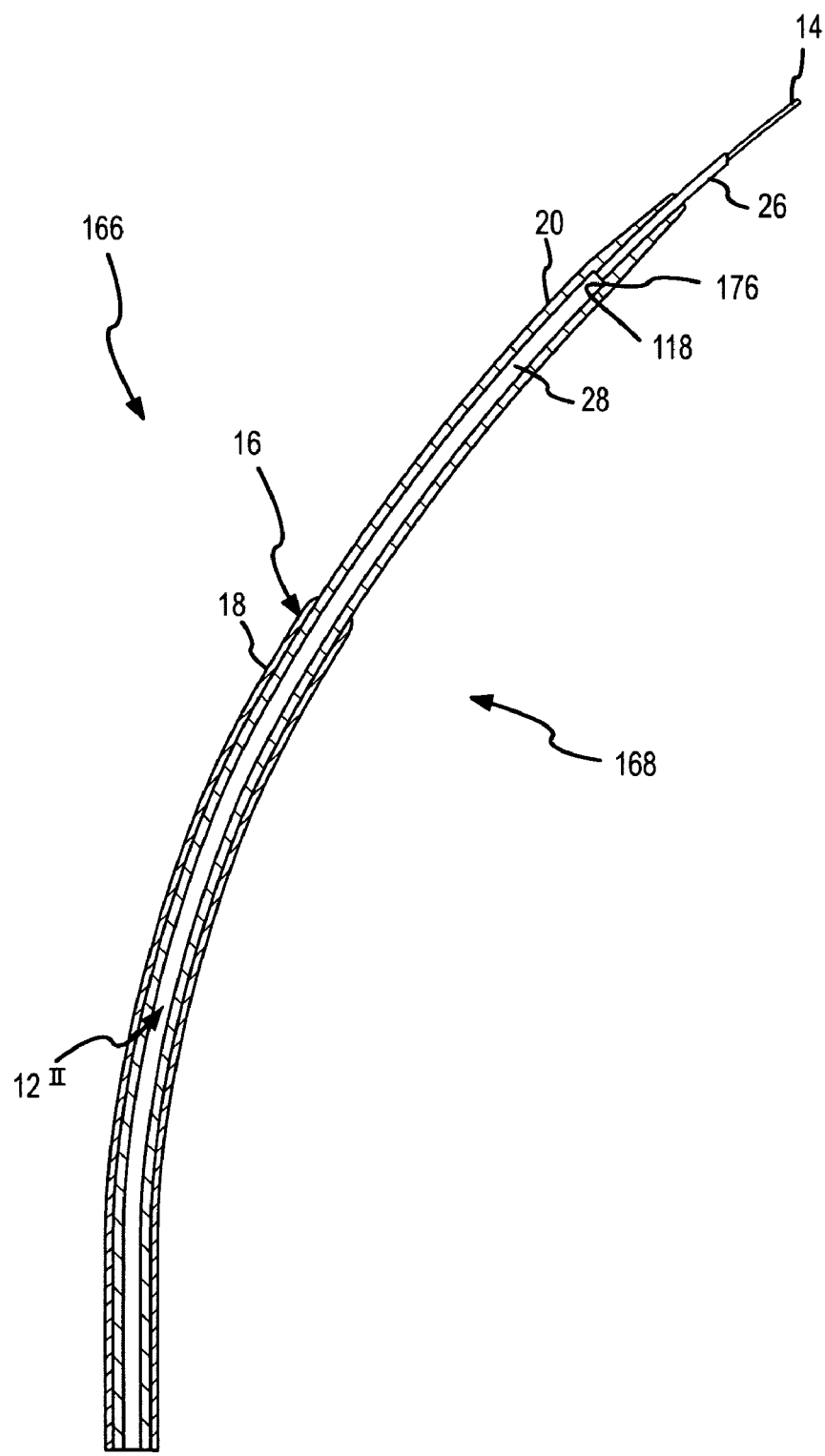
FIG. 25 is a fragmentary, cross-sectional view similar to FIG. 23, but depicting the curved transseptal puncture needle fully inserted against the annular needle stop of the curved transseptal introducer.

FIGS. 23-25 depict a curved transseptal puncture needle 12$^{II}$ having the needle tip 182 depicted in FIGS. 17-22 and an axial orientation according to the second embodiment of the present invention being inserted through the curved transseptal introducer 16. As shown to best advantage in FIG. 24, in the second embodiment of the invention, the axial orientation of the curved portion of the transseptal puncture needle 12$^{III}$ is such that the puncture tip leading edge 192 is adjacent to the inner surface 180 of the dilator 20 on the convex side 166 of the introducer 16. Nevertheless, since the puncture tip leading edge 192 of this needle tip 182 is at the inner surface 114 (FIG. 4) rather than the outer surface 116 of the inner needle tube 26, the puncture tip leading edge 192 is displaced or inwardly offset from the inner surface 180 of the dilator 20. Thus, the puncture tip leading edge 192 is less likely to scrape particulate material from the inner surface of the dilator 20 as the transseptal puncture needle 12$^{II}$ is inserted through the introducer 16. In FIG. 25, the transseptal puncture needle 12$^{II}$ according to the second embodiment of the present invention has been fully inserted into the introducer 16 until the distal end 118 of the outer needle tube 28 rests against the annular needle stop 176, thereby preventing the transseptal puncture needle 12$^{II}$ from being over-inserted through the introducer 16. FIG. 25 thus represents the configuration of the transseptal puncture needle assembly (i.e., transseptal puncture needle 12$^{II}$ and the stylet 14) and the introducer 16 shortly after the inner atrial septum (not shown) has been punctured.

Figures 26, 27:
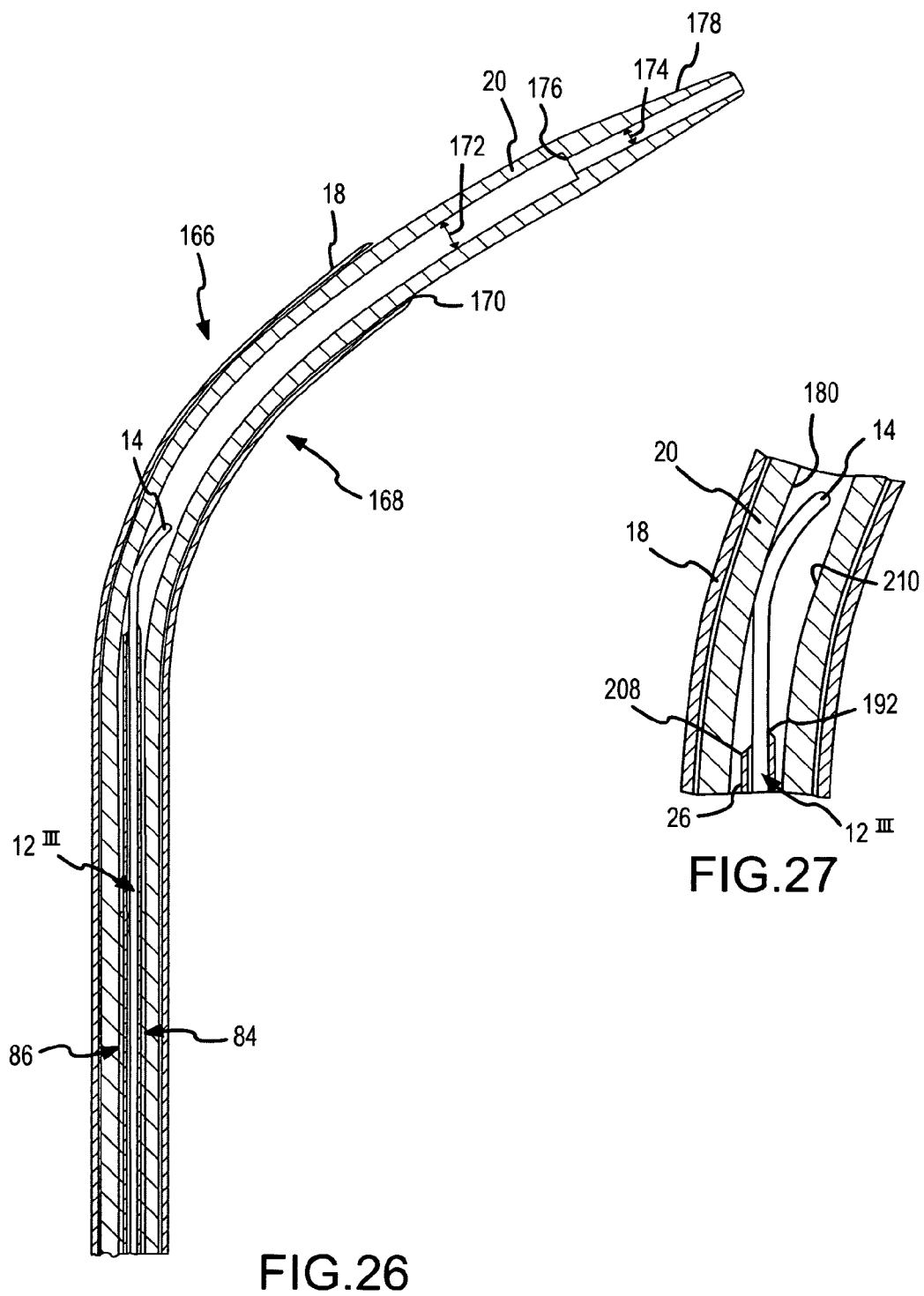
FIG. 26 is a fragmentary, cross-sectional view of a curved transseptal puncture needle having the tip depicted in FIGS. 17-22 and an axial orientation according to the third embodiment of the present invention, when partially inserted through a curved transseptal introducer.
FIG. 27 is an enlarged, fragmentary cross-sectional view of a portion of FIG. 26 to better show the interaction between the puncture tip leading edge and the inner surface of the dilator.
Figure 29:
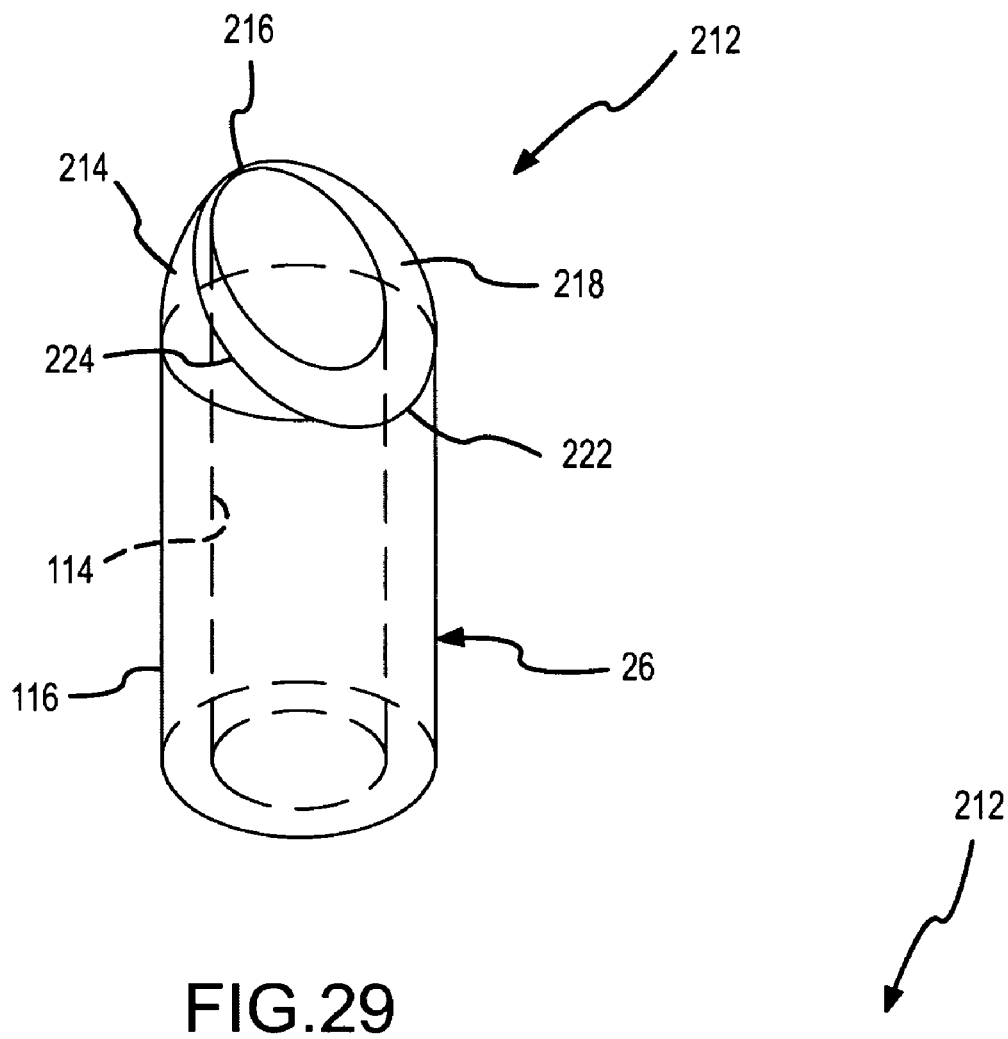
FIG. 29 is an enlarged, isometric view of a needle tip with a conical reverse bevel configuration used in a fourth embodiment and a fifth embodiment of the present invention.
Figure 30:
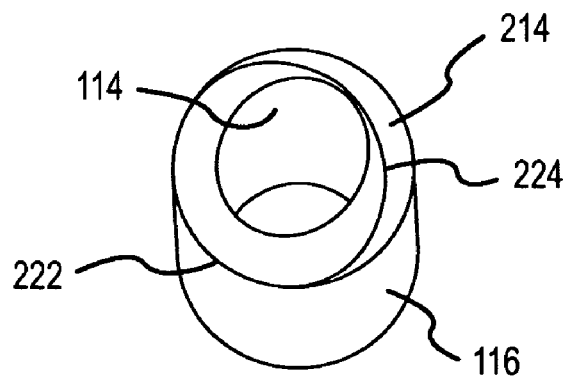
FIG. 30 is a second enlarged, isometric view of the needle tip depicted in FIG. 29.
Figure 28:
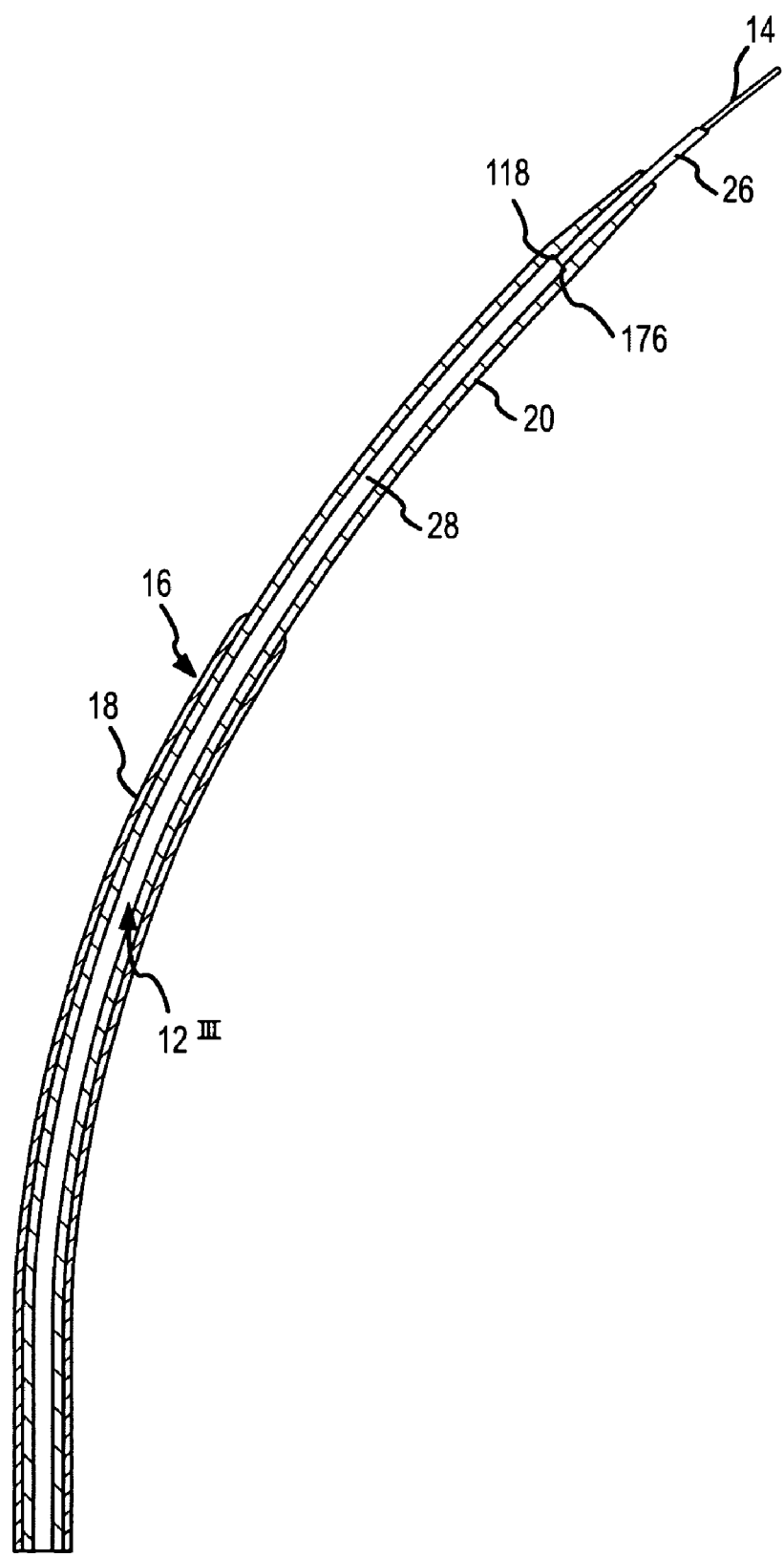
FIG. 28 is a fragmentary, cross-sectional view similar to FIG. 26, but depicting the curved transseptal puncture needle fully inserted against the annular needle stop of the curved transseptal introducer.

Referring next to FIGS. 26-28, the curved transseptal puncture needle according to the third embodiment 12$^{III}$ of the present invention is described next. This third embodiment of the present invention uses the needle tip 182 depicted in FIGS. 17-22 with an axial orientation that is 180° offset from the axial orientation depicted in FIGS. 23-25. Thus, as clearly shown in FIG. 27, the puncture tip leading edge 192 ends up closer to the inner surface 210 of the dilator 20 adjacent to the concave side 168 of the introducer 16 rather than adjacent to the convex side 166 of the introducer 16. As a result, with the orientation depicted in FIGS. 26-28, the needle tip 182 is even less likely to scrape particulate material from the inner surface of the dilator 20 than it is with the orientation depicted in FIGS. 23-25, even though these two embodiments use the same needle tip 182.

FIG. 28 depicts the transseptal puncture needle 12$^{III}$ fully installed in the introducer 16, with the distal end 118 of the outer needle tube 28 of the transseptal puncture needle 12$^{III}$ seated against the annular needle stop 176 (see also FIG. 26) on the inner surface of the dilator 20. FIG. 28 depicts, therefore, the inner needle tube 26 of the transseptal puncture needle 12$^{III}$ extending its maximum amount from the frustal or tapered distal end 178 (FIG. 26) of the dilator 20. Assuming that, in this configuration, the inter-atrial septum has been punctured, the next step would be to advance the dilator 20 and sheath 18 through the puncture in the septum and then to remove the transseptal puncture needle 12$^{III}$ and the dilator 20 to provide lumenal access through the sheath 18 to the left atrium.

FIGS. 29-34 depict a needle tip 212 used in a fourth embodiment 12$^{IV}$ and in a fifth embodiment 12$^{V}$ of the present invention. This needle tip 212 includes a conical reverse bevel 214 to remove all sharp edges except for an upper edge 224 of the conical reverse bevel 214, which serves as a primary cutting edge. The upper edge 224 includes a puncture tip leading edge 216. As in the tip designs discussed above, the needle tip 212 depicted in FIGS. 29-34 also includes a wedge surface 218. The wedge surface 218 is circumscribed or defined by an arcuate edge 222 and the upper edge 224 of the conical reverse bevel 214. In this configuration, however, the remaining edges have been smoothed by the conical reverse bevel 214, which is also designed to move the primary cutting edge or puncture tip leading edge 216 to the inner surface 114 of the inner needle tube 26 of the transseptal puncture needle 12$^{IV}$ or 12$^{V}$. The fact that the puncture tip leading edge 216 is at the inner surface 114 of the inner needle tube 26 is most clearly visible in FIGS. 31 and 33. These two figures show how the conical reverse bevel 214 is used to move the puncture tip leading edge 216 to the inner surface 114 of the inner needle tube 26 of the transseptal puncture needle. FIG. 33 also shows the wedge surface angle 220, which is again approximately 50°, and the puncture tip trailing edge 226. The conical reverse bevel 214 depicted in FIG. 33 has a radius of curvature of, for example, 0.9 mm. As shown, the puncture tip leading edge 216 is tangent to the inner surface 114 of the inner needle tube 26 on the first side 84 of the transseptal puncture needle. The needle tip 212 depicted in FIGS. 29-34 requires penetration force (to cut through, for example, an inter-atrial septum) that is comparable to the penetration force required for the tangential back bevel needle tip 96 depicted in, for example, FIGS. 4-10.

Figures 35, 36:
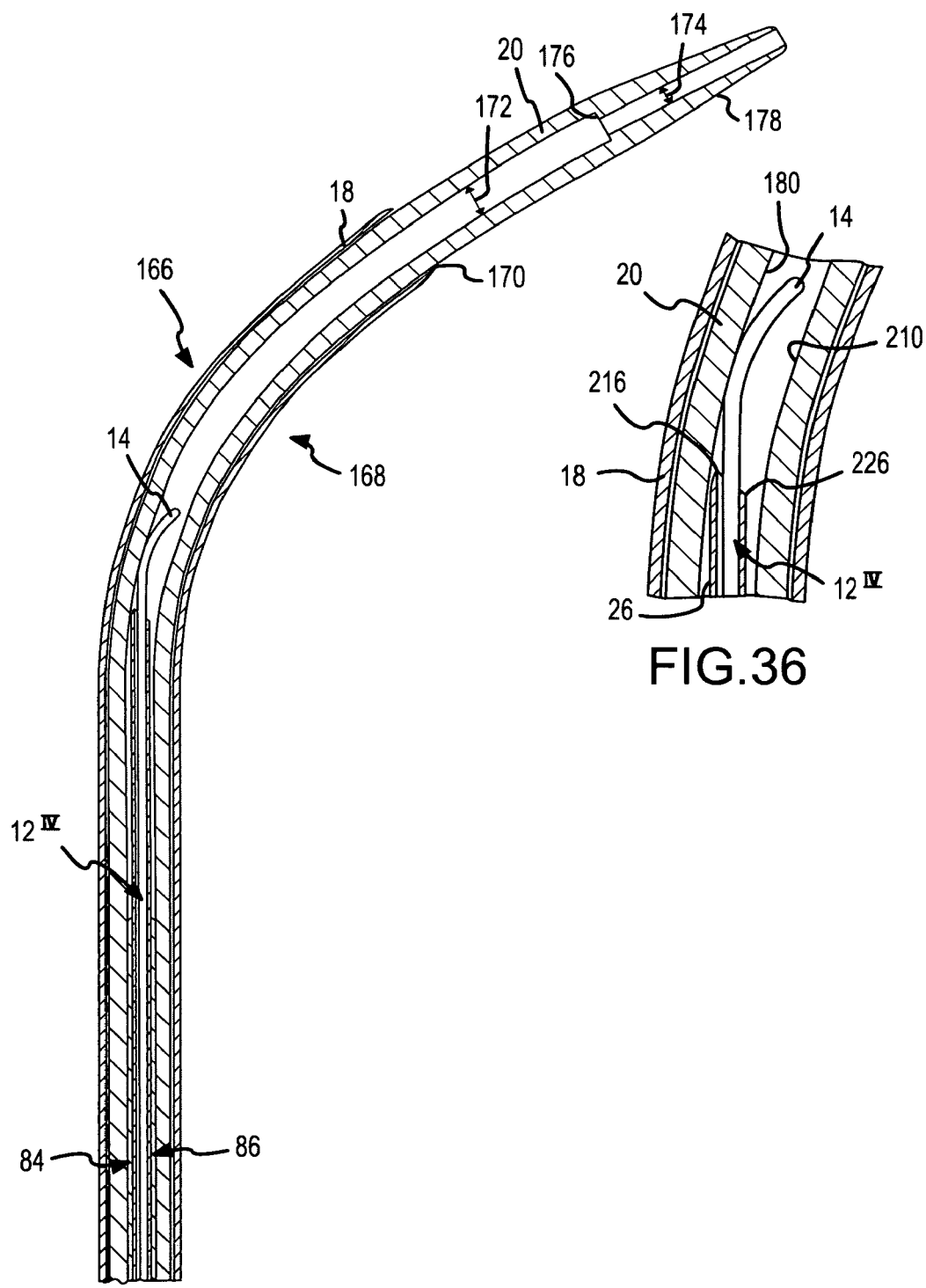
FIG. 35 is a fragmentary, cross-sectional view of a curved transseptal puncture needle having the tip configuration depicted in FIGS. 29-34 and an axial orientation according to the fourth embodiment of the present invention, when partially inserted through a curved transseptal introducer.
FIG. 36 is an enlarged, fragmentary, cross-sectional view of a portion of FIG. 35 to better show the interaction between the puncture tip leading edge and the inner surface of the dilator.
Figure 37:
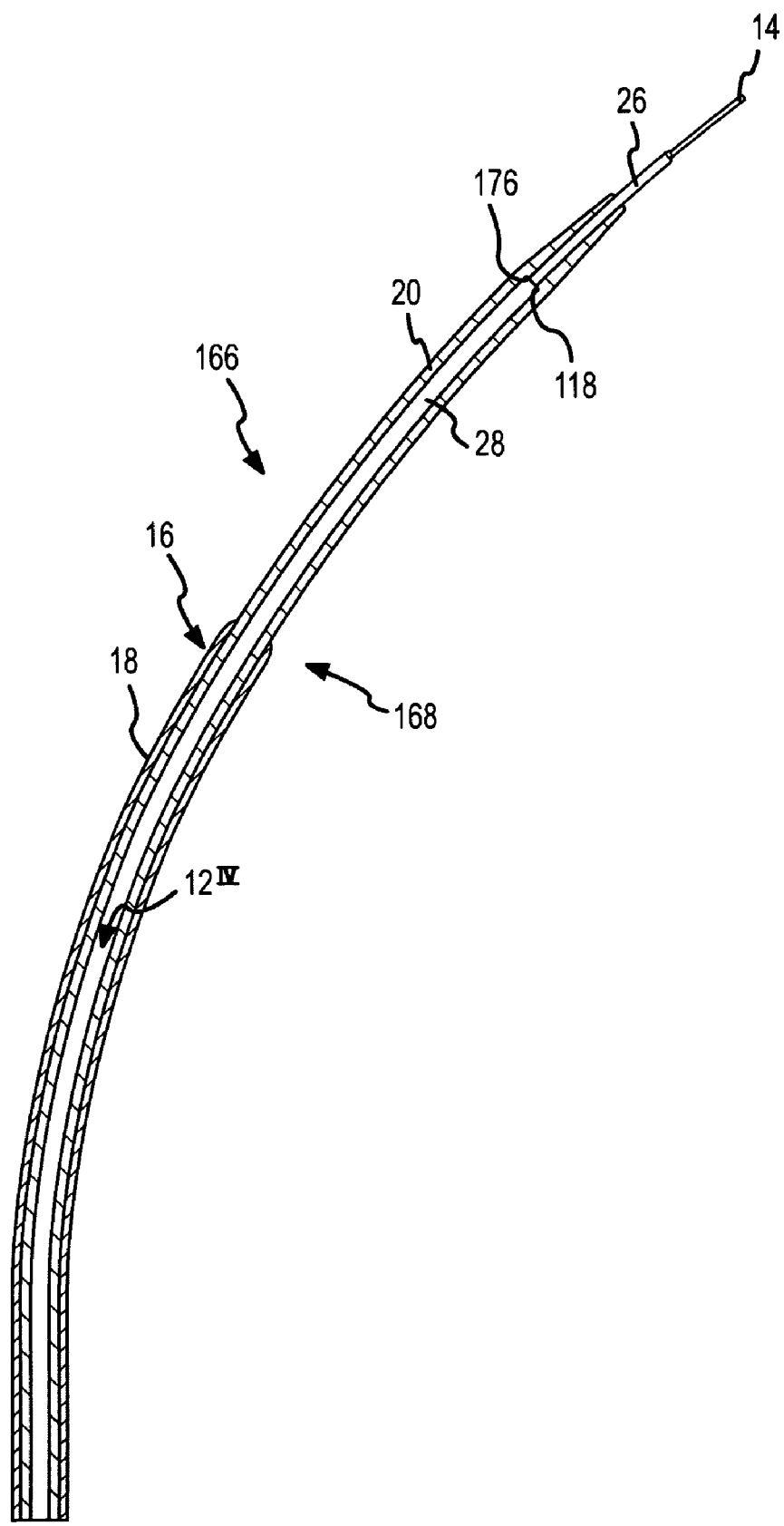
FIG. 37 is a fragmentary, cross-sectional view similar to FIG. 35, but depicting the curved transseptal puncture needle fully inserted against the annular needle stop of the curved transseptal introducer.

Referring next to FIGS. 35-37, the fourth embodiment of a curved transseptal puncture needle 12$^{IV}$ according to the present invention is described next. In the fourth embodiment 12$^{IV}$, the needle tip 212 depicted in FIGS. 29-34 is used. As shown to good advantage in FIGS. 35 and 36, the axial orientation of the transseptal puncture needle 12$^{IV}$ is such that the puncture tip leading edge 216 is adjacent to the inner surface 180 of the dilator 20 on the convex side 166 of the introducer 16. Since the conical reverse bevel 214 offsets the puncture tip leading edge 216 to the inner surface 114 of the inner needle tube 26 of the transseptal puncture needle 12$^{IV}$, there is a reduced opportunity for the puncture tip leading edge 216 to scrape particulate material from the inner surface 180 of the dilator 20. FIG. 37 is a fragmentary, cross-sectional view similar to FIG. 35, but depicting the curved transseptal puncture needle 12$^{IV}$ fully inserted into the introducer 16 until the distal end 118 (see also FIG. 4) of the outer needle tube 28 is seated against the annular needle stop 176 (see also FIG. 35) of the introducer 16.

As previously discussed, the introducer 16 and the transseptal puncture needle 12$^{IV}$ may be configured such that a desired configuration for the resulting assembly of the fully-assembled transseptal puncture needle and introducer has a slightly straighter or less curved configuration than that of the curved transseptal introducer 16 prior to insertion of the transseptal puncture needle 12$^{IV}$. This relationship between the curvature of the introducer 16 alone (e.g., FIG. 35) compared with the curvature of the introducer with the fully inserted transseptal puncture needle (e.g., FIG. 37) may be used to manipulate the frustal or tapered distal end 178 of the dilator 20, and thus the needle tip 212, into a desired position within the heart.

Figures 38, 39:
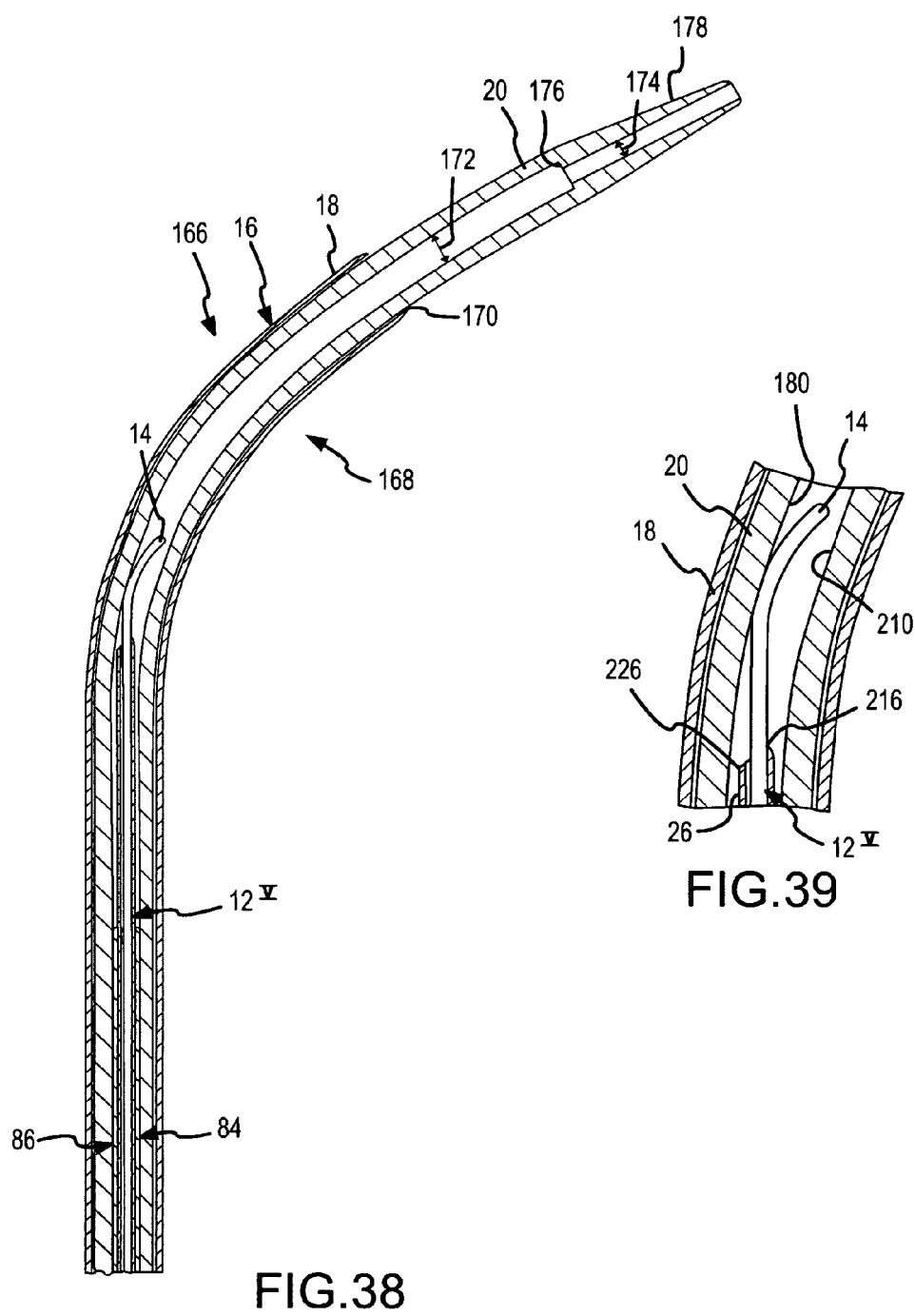
FIG. 38 is a fragmentary, cross-sectional view of a curved transseptal puncture needle having the tip configuration depicted in FIGS. 29-34 and an axial orientation according to the fifth embodiment of the present invention, when partially inserted through a curved transseptal introducer.
FIG. 39 is an enlarged, fragmentary, cross-sectional view of a portion of FIG. 38 to better show the interaction between the puncture tip leading edge and the inner surface of the dilator.
Figure 40:
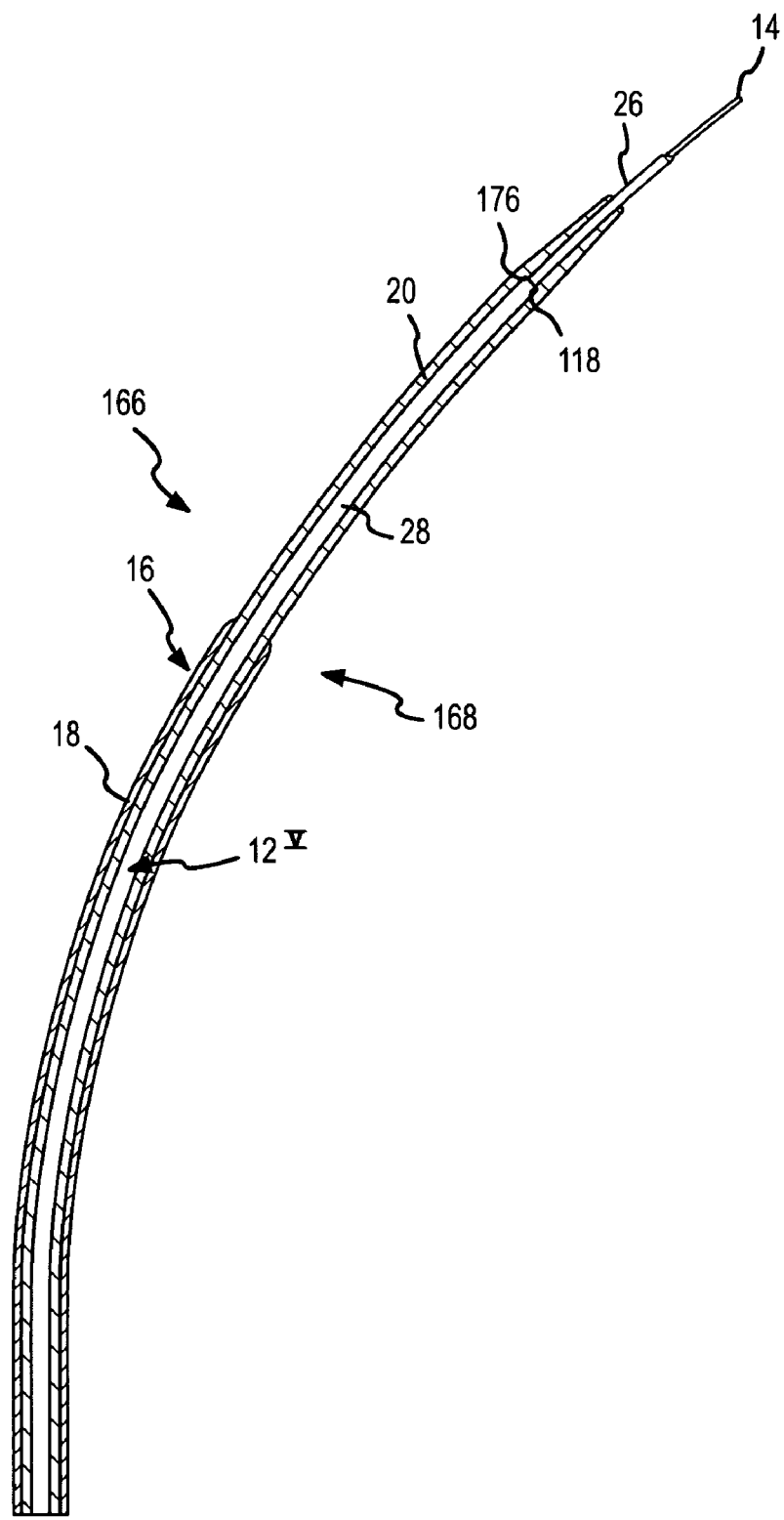
FIG. 40 is a fragmentary, cross-sectional view similar to FIG. 38, but depicting the curved transseptal puncture needle fully inserted against the annular needle stop of the curved transseptal introducer.

FIGS. 38-40 depict a transseptal puncture needle 12$^{V}$ according to a fifth embodiment of the present invention. In particular, as best shown in FIGS. 38 and 39, the fifth embodiment of the present invention uses the needle tip 212 depicted in FIGS. 29-34 with an axial orientation that is offset 180° from the axial orientation of the needle 12$^{IV}$ depicted in FIGS. 35-37. With this tip 212 and this axial orientation, the puncture tip leading edge 216 is adjacent to the inner surface 210 of the dilator 20 on the concave side 168 of the introducer 16 during insertion of the transseptal puncture needle 12$^{V}$ through the introducer 16, as may be seen to best advantage in FIG. 39. Thus, not only does the tip 212 depicted in FIGS. 29-34 require low force to cut through, for example, the inter-atrial septum, but also, with the axial configuration depicted to good advantage in FIGS. 38 and 39, the puncture tip leading edge 216 is unlikely to contact the inner surface of the dilator 20. It is, therefore, also unlikely to scrape particulate material from the dilator 20 that could enter the patient's heart and blood stream. The puncture tip leading edge 216 is unlikely to contact the inner surface of the dilator 20 both since the puncture tip leading edge 216 is at the inner surface 114 of the inner needle tube 26 and since the puncture tip leading edge 216 is on the concave side 168 of the introducer 16 during insertion of the transseptal puncture needle 12$^{V}$ through the introducer 16. FIG. 40 is a fragmentary, cross-sectional view similar to FIG. 38, but depicting the curved transseptal puncture needle 12$^{V}$ fully inserted through the introducer 16 until the distal end 118 (see also FIG. 4) of the outer needle tube 28 is against the annular needle stop 176 (see also FIG. 38) at the step down portion of the dilator inner wall.

Although five embodiments of this invention have been described with a certain degree of particularity, those skilled in the art could make numerous alterations to the disclosed embodiments without departing from the spirit or scope of this invention. For example, additional bevel configurations could be used to offset the puncture tip leading edge (e.g., 192 and 216) toward the inner surface 114 of the inner needle tube 26. As the curvature of the introducer 16 becomes more acute, it becomes more important that the puncture tip leading edge is at the inner surface 114 of the inner needle tube 26 of the transseptal puncture needle and that the puncture tip leading edge (e.g., 192 and 216) is axially oriented to be on the concave side 168 of the introducer 16 as the transseptal puncture needle is inserted through the introducer 16. Desirably, these objectives are achieved while keeping the force required to puncture the septum between the left atrium and the right atrium, for example, low enough that the procedure can be safely performed. It is also desirable that any coring of the punctured tissue be minimized. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A curved transseptal needle assembly-comprising:
a curved needle comprising a concave side, a convex side, and a needle tip;
wherein said needle tip has a leading edge;
wherein said leading edge of said needle tip is oriented along one of said concave side and said convex side of said curved needle; and
wherein said leading edge of said needle tip is located at a distal end of an inner needle tube having an inner surface and an outer surface, and wherein said leading edge of said needle tip is located away from said outer surface of said inner needle tube and adjacent to said inner surface of said inner needle tube.

2. The curved transseptal needle assembly according to claim 1, wherein said needle tip has a reverse tangential back bevel configuration comprising
a first tangential back bevel,
a second tangential back bevel, and
a puncture tip offset bevel, wherein said puncture tip offset bevel moves said puncture tip leading edge to said inner surface of said inner needle tube.

3. The curved transseptal needle assembly according to claim 1, wherein said needle tip geometry is shaped to have smooth surfaces except for a primary cutting edge.

4. The curved transseptal needle assembly according to claim 3, wherein said needle tip has a conical reverse bevel configuration.

5. A device for use by individuals performing specialized invasive techniques, said device comprising
(i) a curved transseptal puncture needle comprising
a first side,
a second side offset from said first side by 180°, and
a needle tip comprising
a puncture tip leading edge;
a puncture tip trailing edge; and
a wedge surface extending between said puncture tip leading edge and said puncture tip trailing edge,
wherein said needle tip has a needle tip configuration selected from the group consisting of a reverse tangential back bevel and a conical reverse bevel; and
(ii) a curved transseptal introducer through which said curved transseptal puncture needle is inserted, said curved transseptal introducer comprising a convex side; and
a concave side offset from said convex side by 180°, wherein said curved transseptal puncture needle has an axial orientation relative to said curved transseptal introducer.

6. The device of claim 5 further comprising a stylet.

7. The device of claim 5, wherein said curved transseptal puncture needle further comprises a needle tip length, said needle tip length being a distance measured from said puncture tip leading edge to said puncture tip trailing edge in a direction parallel to a centerline of said curved transseptal puncture needle.

8. The device of claim 5, wherein said curved transseptal introducer further comprises a sheath.

9. The device of claim 8, wherein said introducer further comprises a dilator with an extended portion extending from a distal end of said sheath.

10. The device of claim 9, wherein said extended portion of said dilator necks down, from a first internal diameter to a second internal diameter, creating an annular needle stop on an inner surface of said dilator.

11. The device of claim 10 further comprising a needle distal end, wherein said needle distal end comprises a working portion including an inner needle tube conjoined with an outer needle tube, wherein said outer needle tube comprises a proximal end and a distal end, and wherein said distal end of said outer needle tube is adapted to seat against said annular needle stop when said curved transseptal puncture needle is fully inserted into said curved transseptal introducer.

12. The device of claim 10, wherein said dilator includes a tapered distal end.

13. The device of claim 9, wherein said dilator has an inner surface, and wherein said axial orientation of said curved transseptal puncture needle is such that said puncture tip leading edge is adjacent to said inner surface of said dilator on said convex side of said introducer.

14. The device of claim 9, wherein said dilator has an inner surface, and wherein said axial orientation of said curved transseptal puncture needle is such that said puncture tip leading edge is adjacent to said inner surface of said dilator on said concave side of said introducer.

15. The device of claim 5, wherein axial orientation of said curved transseptal puncture needle relative to said curved transseptal introducer is such that said first side of said curved transseptal puncture needle is on said concave side of said curved transseptal introducer.

16. The device of claim 5, wherein axial orientation of said curved transseptal puncture needle relative to said curved transseptal introducer is such that said first side of said curved transseptal puncture needle is on said convex side of said curved transseptal introducer.

17. The device of claim 5 further comprising a needle distal end, wherein said needle distal end comprises a working portion including an inner needle tube and an outer needle tube, wherein said inner needle tube and said outer needle tube are conjoined, wherein said inner needle tube comprises a proximal end and a distal end, wherein said outer needle tube comprises a proximal end and a distal end, wherein said proximal end of said inner needle tube is inserted into said distal end of said outer needle tube, creating an inner needle tube embedded portion and an inner needle tube exposed portion, and creating an outer needle tube circumscribing portion and an outer needle tube nonoverlapping portion, and wherein said conjoined inner and outer needle tubes define a conjoined outer surface including an outer surface of said outer needle tube plus an outer surface of said exposed portion of said inner needle tube.

18. The device of claim 17, wherein said inner needle tube further comprises an inner tube inner surface, an inner tube outer diameter, and a frustal entrance surface extending from said inner tube inner surface to said proximal end of said inner needle tube, a juncture between said frustal entrance surface of said inner needle tube and said proximal end of said inner needle tube thereby defining an inner tube entrance diameter that is smaller than said inner tube outer diameter.

19. The device of claim 18, wherein said frustal entrance surface forms an entrance angle of 60°.

20. The device of claim 17, wherein said outer needle tube further comprises an outer tube inner surface, an outer tube outer diameter, and a frustal entrance surface extending from said outer tube inner surface to said proximal end of said outer needle tube, a juncture between said frustal entrance surface of said outer needle tube and said proximal end of said outer needle tube thereby defining an outer tube entrance diameter that is smaller than said outer tube outer diameter.

21. The device of claim 20, wherein said frustal entrance surface forms an entrance angle of 60°.

22. The device of claim 17, wherein said embedded portion of said inner needle tube is 83 mm long and is secured within said outer needle tube by adhesive.

23. The device of claim 17, wherein said outer needle tube circumscribing portion extends around said inner needle tube embedded portion, and wherein said outer needle tube non-overlapping portion is a remainder of said outer needle tube.

24. The device of claim 17, wherein said distal end of said outer needle tube is blunt with rounded edges.

25. The device of claim 17, wherein said inner needle tube embedded portion is 83 mm long.

26. The device of claim 17, wherein said inner needle tube embedded portion is secured within said outer needle tube circumscribing portion with adhesive.

27. The device of claim 26, wherein said adhesive is applied to approximately 68 mm of said inner needle tube embedded portion.

28. The device of claim 17, wherein said conjoined inner and outer needle tubes are united with a mounting collar.

29. The device of claim 28, wherein said conjoined inner and outer needle tubes are press fit into said mounting collar.

30. The device of claim 28, wherein a shield is attached between said proximal end of said outer needle tube and said mounting collar.

31. The device of claim 30, wherein said shield comprises a shield point, and wherein said shield point indicates a direction of curvature of said curved transseptal puncture needle.

32. The device of claim 28, wherein said conjoined inner and outer needle tubes comprise a needle exposed portion having a first length, wherein said needle exposed portion is that portion of said conjoined inner and outer needle tubes extending from said mounting collar.

33. The device of claim 32, wherein said inner needle tube comprises an exposed portion having a second length.

34. The device of claim 33, wherein said second length is about 15±0.2 mm.

35. The device of claim 33, wherein said exposed portion of said inner needle tube is straight.

* * * * *

UNITED STATES PATENT AND TRADEMARK OFFICE
CERTIFICATE OF CORRECTION

| | | |
|---|---|---|
| PATENT NO. | : 7,635,353 B2 | Page 1 of 1 |
| APPLICATION NO. | : 10/947817 | |
| DATED | : December 22, 2009 | |
| INVENTOR(S) | : Ravisankar Gurusamy et al. | |

It is certified that error appears in the above-identified patent and that said Letters Patent is hereby corrected as shown below:

Column 17, claim 5, line 44 after comprising, kindly start a new paragraph.

Signed and Sealed this
Twelfth Day of March, 2013

Teresa Stanek Rea
*Acting Director of the United States Patent and Trademark Office*